United States Patent [19]

Shindo et al.

[11] Patent Number: 5,327,191
[45] Date of Patent: Jul. 5, 1994

[54] EYE DIRECTION DETECTING APPARATUS

[75] Inventors: Osamu Shindo; Shigeo Toji, both of Tokyo, Japan

[73] Assignee: Asahi Kogaku Kogyo Kabushiki Kaisha, Tokyo, Japan

[21] Appl. No.: 982,427

[22] Filed: Nov. 27, 1992

Related U.S. Application Data

[63] Continuation of Ser. No. 576,191, Aug. 27, 1990, abandoned, which is a continuation of Ser. No. 282,035, Dec. 9, 1988, abandoned, which is a continuation-in-part of Ser. No. 152,359, Feb. 4, 1988, abandoned.

[30] Foreign Application Priority Data

Jun. 11, 1987 [JP] Japan .................. 62-146067
May 20, 1988 [JP] Japan .................. 63-123562
Jun. 10, 1988 [JP] Japan .................. 63-143259
Dec. 17, 1988 [JP] Japan .................. 63-319337

[51] Int. Cl.⁵ .............................. G03B 13/36
[52] U.S. Cl. ................................ 354/402; 354/410
[58] Field of Search ............ 354/400, 402, 403, 404, 354/407, 162-166, 62, 410

[56] References Cited

U.S. PATENT DOCUMENTS

| Re. 31,370 | 9/1983 | Mashimo et al. ............ 354/23 D |
| 3,543,666 | 12/1970 | Kazel .................... 354/404 |
| 3,701,309 | 10/1972 | Thiele et al. . | |
| 3,712,716 | 1/1973 | Cornsweet et al. ............ 351/7 |
| 3,724,932 | 4/1973 | Cornsweet et al. ............ 351/7 |
| 3,804,496 | 4/1974 | Crane et al. ................ 351/6 |
| 4,047,187 | 9/1977 | Mashimo et al. ............ 354/23 D |
| 4,183,642 | 1/1980 | Fukuoka ................... 354/25 |
| 4,287,410 | 9/1981 | Crane et al. . | |
| 4,445,757 | 5/1984 | Enomoto et al. . | |
| 4,508,443 | 4/1985 | Matsuzaki et al. . | |
| 4,574,314 | 3/1986 | Weinblatt ................ 354/400 |
| 4,636,624 | 1/1987 | Ishida et al. . | |
| 4,786,934 | 11/1988 | Kunze et al. ............ 354/409 |
| 4,836,670 | 6/1989 | Hutchinson ............... 354/62 |

(List continued on next page.)

FOREIGN PATENT DOCUMENTS 0055338 7/1982 European Pat. Off. .

(List continued on next page.)

OTHER PUBLICATIONS

Two German Office Actions.
Patent Abstracts of Japan, P-306, Oct. 5, 1984, vol. 8, No. 219.
G. Schroder, "Techische Optik Kurz und bundig", Vogel-Verlag 1974, p. 41, and English translation.
European Search Report and Annex.
Methods and Design-Survey of Eye Movement Recording Methods, by Young and Sheena, *Behavior Research Methods and Instrumentation*, pp. 397–429 (vol. 7(5), 1975.
"Psychological Physic of Vision," by Mitsuo Ikeda, 1975.
"Fixation Point Measurement by the Oculometer Technique," *Optical Engineering*, Jul./Aug. 1974, pp. 339–342.

Primary Examiner—Russell E. Adams
Attorney, Agent, or Firm—Sandler, Greenblum & Bernstein

[57] ABSTRACT

An eye direction detecting apparatus for a camera having a light transferring system for guiding a beam of parallel light rays to an eye of a photographer includes a light receiving system having a light receiving portion on which a first Purkinje image based on specular reflection of a cornea of the eye and reflecting light from a retina of the eye is formed, the light receiving portion generating a light receiving output. The apparatus further includes a processing circuit for detecting the eye direction of the eye based on the light receiving output of the light receiving portion. Further, according to the teachings of the present invention, including an optical member having certain identically inclined surfaces prevents refracted light from forming a ghost image within the light receiving system of an eye direction detecting apparatus.

94 Claims, 23 Drawing Sheets

U.S. PATENT DOCUMENTS

| | | | |
|---|---|---|---|
| 4,857,720 | 8/1989 | Karasaki | 250/201 |
| 4,974,010 | 11/1990 | Cleveland et al. | 354/403 |
| 5,017,005 | 5/1991 | Shindo | 356/125 |
| 5,036,347 | 7/1991 | Tsunekawa et al. | |

FOREIGN PATENT DOCUMENTS

| | | |
|---|---|---|
| 1211815 | 3/1966 | Fed. Rep. of Germany . |
| 1930007 | 1/1970 | Fed. Rep. of Germany . |
| 3329603 | 3/1984 | Fed. Rep. of Germany . |
| 3331264 | 3/1984 | Fed. Rep. of Germany . |
| 3336265 | 4/1984 | Fed. Rep. of Germany . |
| 3505864 | 8/1985 | Fed. Rep. of Germany . |
| 2382056 | 9/1978 | France . |
| 40-26379 | 11/1965 | Japan . |
| 59-102202 | 6/1984 | Japan . |
| 60-32012 | 2/1985 | Japan . |
| 60-41013 | 3/1985 | Japan . |
| 60-174132 | 9/1985 | Japan . |
| 61-172552 | 8/1986 | Japan . |
| 62-47612 | 3/1987 | Japan . |
| 62-189415 | 8/1987 | Japan . |
| 1277533 | 11/1988 | Japan . |
| 1241511 | 9/1989 | Japan . |
| 1-274736 | 11/1989 | Japan . |
| 1412707 | 11/1975 | United Kingdom . |
| 8701571 | 3/1987 | World Int. Prop. O. . |

FIG. 28
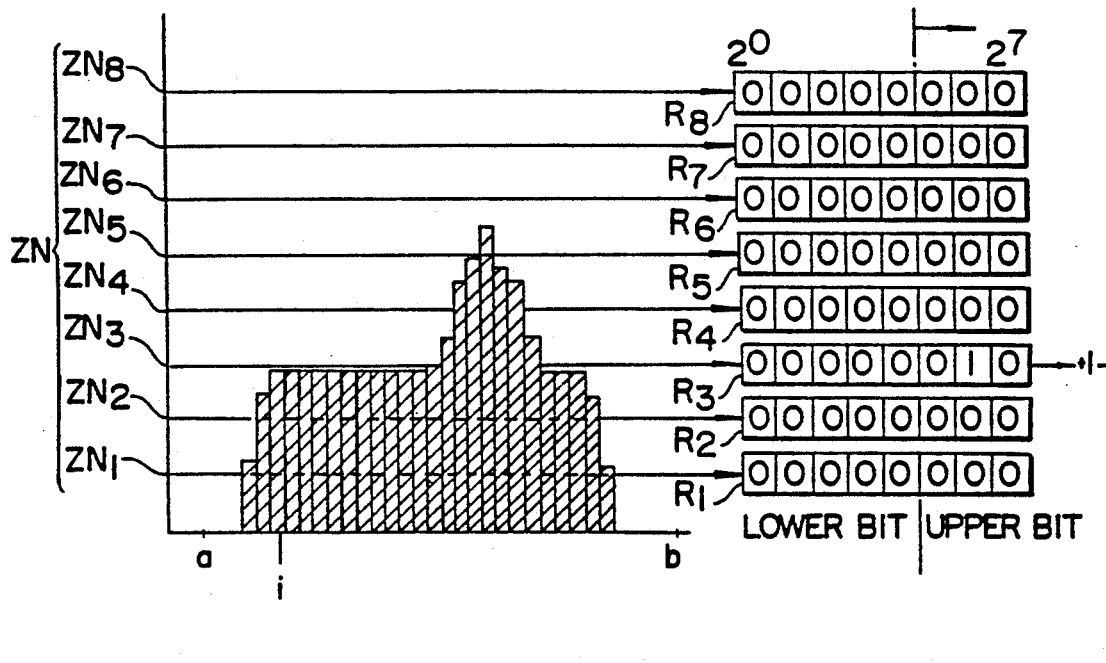
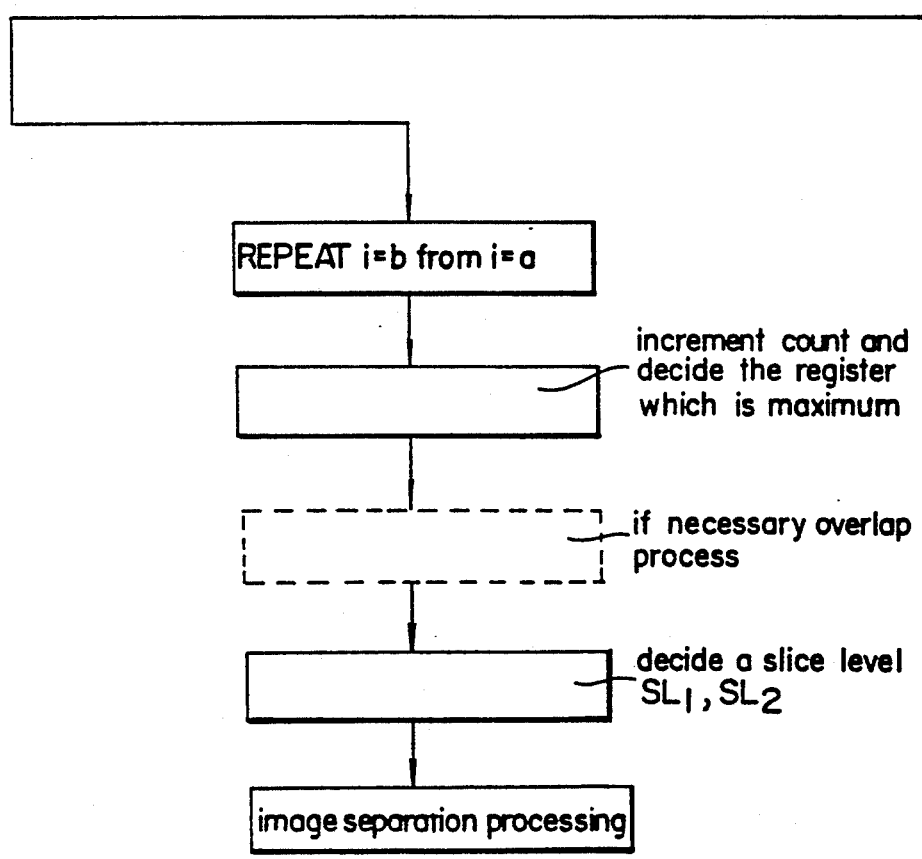

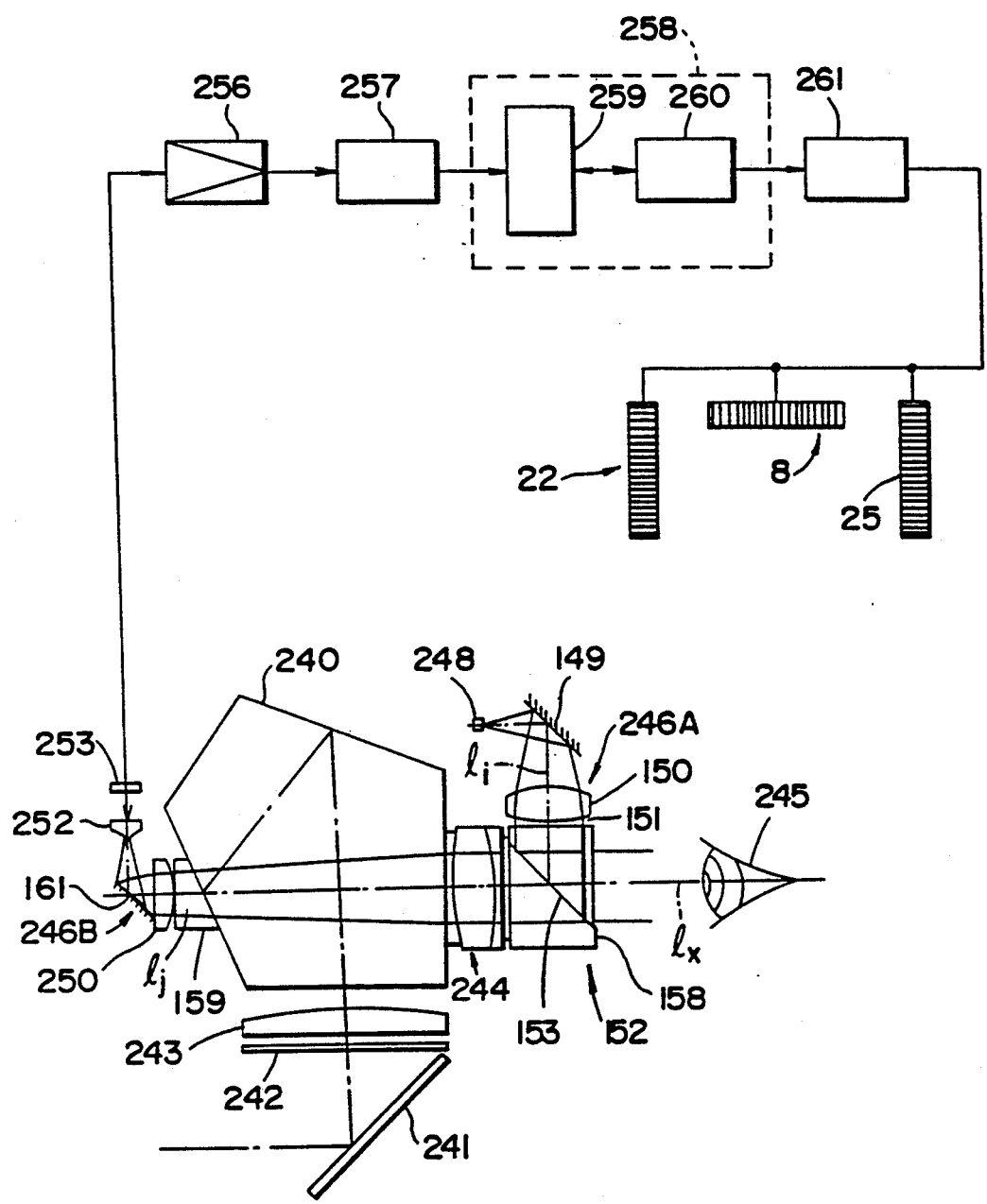
FIG_ 33

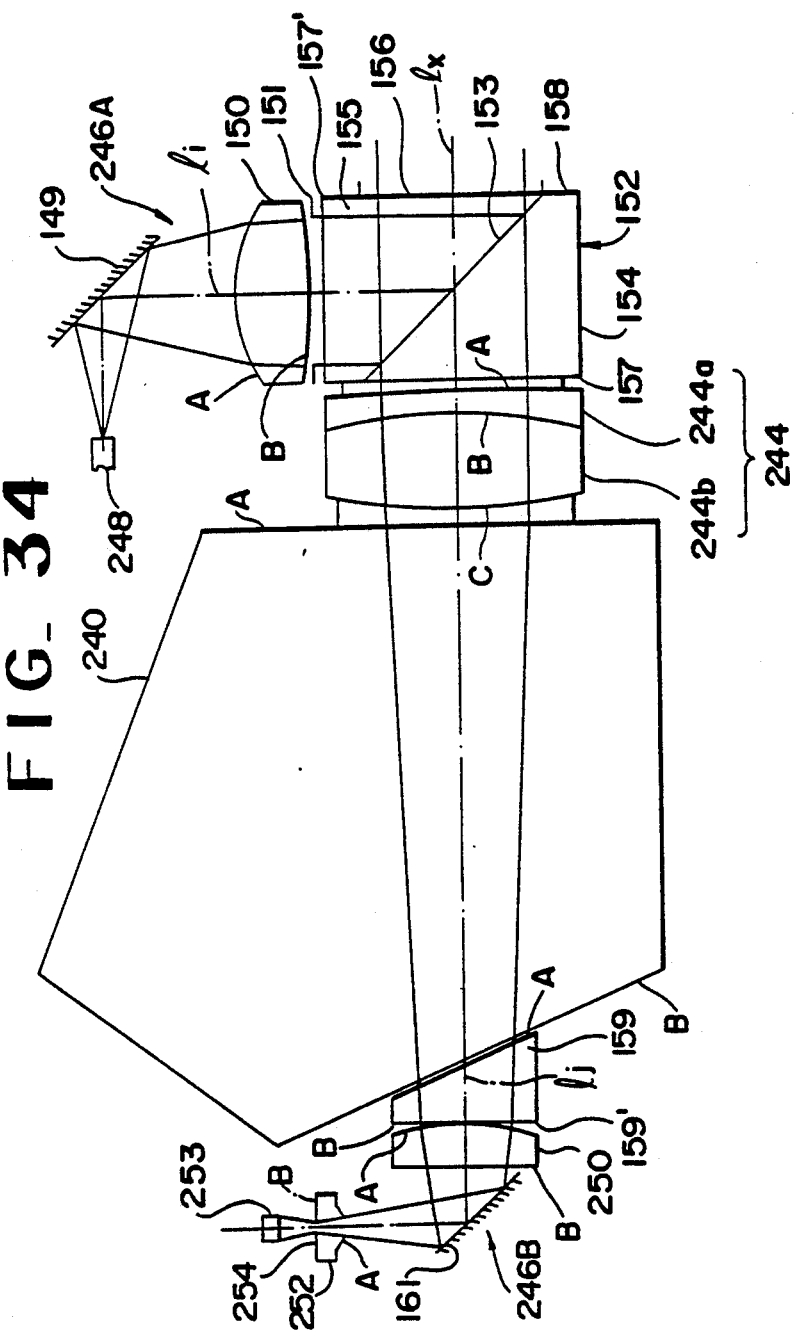

FIG_38

EYE DIRECTION DETECTING APPARATUS

This application is a continuation of application Ser. No. 07/576,191, filed Aug. 27, 1990, now abandoned which is a continuation of application Ser. No. 07/282,035, filed on Dec. 9, 1988, now abandoned, which is a continuation-in-part of application Ser. No. 07/152,359, filed on Feb. 4, 1988, now abandoned.

The disclosure of application Ser. No. 07/152,359 is expressly incorporated in its entirety by reference herein.

BACKGROUND OF THE INVENTION

1. Field of the Invention

The present invention relates to an eye direction detecting apparatus. More particularly, the present invention relates to an eye direction detecting apparatus suitable for use in a camera having an automatic focusing device in which focusing zones of an auto focus optical system, each of which focusing zones corresponds to each of various focusing zones of the finder, are located in optically generally conjugate positions with a plurality of focusing zones disposed within a view field of the finder, and focusing is made on an object which is visually overlapped with a focusing zone corresponding to a selected one of the various focusing zones of the finder.

2. Description of Related Art

An auto optical focus detecting device for a camera having an auto focus optical system has heretofore been developed. FIG. 1 is a schematic view showing an optical system of an auto optical focus detecting device of, for example, which has an auto focus optical system. In the figure, 1 denotes a photographic lens, 2 a subject to be photographed, 3 a view field mask, 4 a condenser lens, 5 a diaphragm mask, 6 and 7 a separator lens serving as an image splitting optical element for reimaging, and 8 a CCD serving as an image receiving element. The view field mask 3, the condenser lens 4, the diaphragm mask 5, the separator lenses 6 and 7, and the CCD 8 are integrally modulated as one unit and constitute an auto focus optical system 9.

In this auto focus optical system 9, the view field mask 3 is disposed in the vicinity of a film equivalent plane 10. The film equivalent plane 10 is in a position optically conjugate with the subject 2 to be photographed through the photographic lens 1. A well focused image 11 of the subject 2 is formed on the film equivalent plane 10 when the photographic lens 1 is in focus. The condenser lens 4 and the diaphragm mask 5 have the function of splitting the photographic light passing on both right and left sides of the photographic lens 1. The separator lenses 6 and 7 are in a position optically conjugate with the photographic lens 1 through a condenser lens 4.

The separator lenses 6 and 7, as shown in FIG. 2, are disposed in the horizontal direction. Further, the separator lenses 6 and 7 face imaginary opening areas 14 and 15 of an exit pupil 13 of the photographic lens 1 through a zone 12 located in a position optically conjugate with a center zone of a finder as will be described. The separator lenses 6 and 7 intake a bundle of light rays passed through the opening areas 14 and 15. The image 11 formed on the film equivalent plane 10 is reimaged as images 11' in two areas on the CCD 8.

Distance between the images 11' well focused (see FIG. 3(a)) is represented by $l_o$ as shown in FIG. 4.

When the photographic lens 1 is focused in a position in front of the focal point of the aforementioned well focused image as shown in FIG. 3(b), the distance between the images 11' becomes less and, as a result, the distance between signals S corresponding thereto becomes less than the distance $l_o$. On the other hand, when the photographic lens 1 is focused in a position behind the focal point of the aforementioned well focused image as shown in FIG. 3(c), the distance between the images 11' becomes greater and, as a result, a distance between signals S corresponding thereto become greater than the distance $l_o$. Since the distance between the images 11' is changed in proportion to a defocusing amount of the photographic lens 1, in the conventional auto optical focus detecting device of a single-lens reflex camera, a distance between images of the CCD 8 is detected and the signals are arithmetically processed, and the photographic lens 1 is moved to the focal position with reference to the focusing direction and defocusing amount of the photographic lens 1. And, as shown for example in FIG. 5, if the optical focus is found by framing such that desired subject 2 to be photographed is located in the center zone 17 arranged at the center of the finder 16, the photographic lens 1 is automatically brought into a focusing state. If a photograph is taken in the foregoing state, a well focused photograph can be obtained.

In this conventional auto optical focus detecting device of a single-lens reflex camera, since the zone is located in the center of the finder 16, a desired subject 2 will be positioned in the center of an obtained photograph unless an adequate alternate arrangement is made. There are, some instances it should be noted, where a desired subject 2 is preferably positioned in a peripheral area of a photograph instead of the center of the photograph. To this end, therefore, in the conventional single-lens reflex camera, a focus lock mechanism is provided. That is, the subject 2 to be photographed is positioned in the center of the finder 16 to automatically find the distance to the subject 2. In that state, the focus is locked. If a photograph is taken in the framing as shown in FIG. 6, a photograph can be obtained in which a desired subject 2 is positioned in the peripheral area.

However, in this conventional auto optical focus detecting device of a single-lens reflex camera, the subject 2 must first be positioned in the center of the finder 16. Then, the photographic lens 1 must be moved to a focusing state. In that state, the focus must be locked to fix the photographic lens 1. Then, the framing must be performed once again. Only thereafter can a photograph be taken. Therefore, much time and labor are required before the camera is ready to take a photograph.

SUMMARY OF THE INVENTION

It is therefore a first object of the present invention (as it is for parent application Ser. No. 07/152,359) to provide an auto optical focus detecting device for a single-lens reflex camera, in which a photographic operation for obtaining a photograph with a desired subject positioned in a peripheral area can be easily and rapidly performed.

In order to achieve the first object, an auto optical focus detecting device for a camera according to the present invention (and according to the invention of parent application Ser. No. 07/152,359) comprises a center zone being located in a center of a view finder of a camera body; at least two peripheral zones being located in the view finder, one of the two peripheral zones being located in the right-hand side with respect to the center zone and the other being located in the left-hand side; the camera body containing a center auto focus system and at least two peripheral auto focus optical systems; the center auto focus optical system having a zone corresponding to the center zone, the zone being substantially conjugate with the center zone; the peripheral auto focus optical systems, respectively, having a substantially conjugate zone corresponding to the peripheral zone, each zone being substantially conjugate with the peripheral zone; a photographic lens being attached to the camera body, an exit pupil of the photographic lens being optically aligned to project light rays through the center zone of the center auto focus optical system, at least two aperture zones being defined on the exit pupil by the at least two peripheral auto focus optical systems, each of the aperture zones being optically aligned to project light rays through the peripheral zone, at least one of the two aperture zones being located at an upper side away from a central portion of the exit pupil and the other being located at a lower side away from the central portion; the center auto focus optical system and the two peripheral auto focus optical systems, respectively, having at least one photoelectronic device for producing an output signal; and the output signal produced by the photoelectronic device being adapted to move the photographic lens automatically, thereby to bring the camera to be in focus.

According to this auto optical focus detecting device, when a photograph with a subject to be photographed positioned in a peripheral area is required, a distance to the subject can be automatically found by using a peripheral&l auto focus optical system adapted to find the distance to the peripheral area without the aforementioned troublesome photographic procedure. Therefore, a photograph can be taken rapidly.

In the invention having the above-mentioned embodiment for achieving the first object, if the separator lens of the peripheral auto focus optical system is not optically aligned with the exit pupil at predetermined angles, the image detecting accuracy of the auto focus optical system becomes poor due to vignetting. Therefore, the angle of the separator lens with respect to the exit pupil of the photographic lens of the peripheral auto focus optical system must be adjusted each time according to the lens characteristic (for example, whether the lens has a short focal point or a long focal point) of a photographic lens mounted on a lens mount which is to be attached to and detached from the camera body.

The fact that the adjustment and/or establishment of the angles for the separator lens of the peripheral auto focus optical system with respect to the exit pupil of the photographic lens depending on whether the photographic lens mounted on the lens mount has a short focal point or a long focal point must be carried out manually causes much inconvenience with respect to standardizing a camera body since various kinds of lens groups are prepared as interchangeable lens mounts which are to be attached to or detached from the camera body.

It is therefore a second object of the present invention (as it is for the invention of parent application Ser. No. 07/152,359) to provide an auto optical focus detecting device of a camera, in which the adjustment and/or establishment of angles can be automatically performed such that a direction of a bundle of light rays taken into the peripheral auto focus optical system is directed toward the exit pupil of the photographic lens according to the attachment of a lens mount to a camera body.

In order to achieve the second object, an auto optical focus detecting device of a single-lens reflex camera according to present invention (and the invention of the parent application Ser. No. 07/152,359) comprises a center zone being located in a center of a view finder of a camera body; at least two peripheral zones being located in the view finder, one of the two peripheral zones being located in the right-hand side with respect to the center zone and the other being located in the left-hand side; the camera body containing a center auto focus optical system and at least two peripheral auto focus optical systems; the center auto focus optical system having a zone corresponding to the center zone, the zone being substantially conjugate with the center zone; the peripheral auto focus optical systems, respectively, having a substantially conjugate zone corresponding to the peripheral zone, each zone being substantially conjugate with the peripheral zone; a photographic lens being attached to the camera body, an exit pupil of the photographic lens being optically aligned to project light rays through the center zone of the center auto focus optical system, at least two aperture zones being defined on the exit pupil by the at least two peripheral auto focus optical systems, each of the aperture zones being optically aligned to project light rays through the peripheral zone, at least one of the two aperture zones being located at an upper side away from a central portion of the exit pupil and the other being located at a lower side away from the central portion; the center auto focus optical system and the two peripheral auto focus optical systems, respectively, having at least one photoelectronic device for producing an output signal; and the output signal produced by the photoelectronic device being adapted to move the photographic lens automatically, thereby to bring the camera into focus, each of the peripheral auto focus optical systems comprising a focus unit, the camera body having at least one optical member which is located in front of the focus unit, and the optical member changing a direction of a bundle of light rays coming through the aperture zone, thus the bundle of light rays coming through the aperture zone being automatically made incident to the zone of each peripheral auto focus optical system according to the photographic lens characteristic.

As another embodiment for achieving the second object, an auto optical focus detecting device of a single-lens reflex camera according to the present invention (and the invention of parent application Ser. No. 07/152,359) comprises a center zone being located in a center of a view finder of a camera body; at least two peripheral zones being located in the view finder, one of the two peripheral zones being located in the right-hand side with respect to the center zone and the other being located in the left-hand side; the camera body containing a center auto focus optical system and at least two peripheral auto focus optical systems; the center auto focus optical system having a zone corresponding to the center zone, the zone being substantially conjugate with the center zone; the peripheral auto focus optical systems, respectively, having a substantially conjugate zone corresponding to the peripheral zone, each zone being substantially conjugate with the peripheral zone;

a photographic lens being attached to the camera body, an exit pupil of the photographic lens being optically aligned to project light rays through the center zone of the center auto focus optical system, at least two aperture zones being defined on the exit pupil by the at least two peripheral auto focus optical systems, each of the aperture zones being optically aligned to project light rays through the peripheral zone, at least one of the two aperture zones being located at an upper side away from a central portion of the exit pupil and the other being located at a lower side away from the central portion; the center auto focus optical system and the two peripheral auto focus optical systems, respectively, having at least one photoelectronic device for producing an output signal; the output signal produced by the photoelectronic device being adapted to move the photographic lens automatically, thereby to bring the camera to be in focus; the each peripheral auto focus optical system comprising a rotatable focus unit containing the camera body, and when a lens mount for the photographic lens being attached to the camera body, the rotatable focus unit being rotated mechanically, thus a bundle of rays coming through the aperture zone being automatically made incident to the zone of each peripheral auto focus optical system according to the photographic lens characteristic.

According to the above-mentioned further embodiment for achieving the second object, even if the photographic lens is replaced with another lens having a different focal distance, the optical axis of the peripheral auto focus optical system can be mechanically and automatically brought to be faced with the center of the exit pupil of the photographic lens by mounting action of the photographic lens to the camera body so as to avoid the problem of vignetting.

Further objects of the present invention (and the invention of parent application Ser. No. 07/152,359) are directed to eye direction detection. For example, a third object of the present invention is to provide an eye direction detecting apparatus for a camera for detecting the eye direction of a photographer.

A fourth object of the present invention is to provide an eye direction detecting apparatus for a camera having an automatic focusing device, in which focusing zones of an auto focus optical system, which correspond to various focusing zones of the finder, are located in optically generally conjugate positions with a plurality of focusing zones disposed within a view field of the finder, and focusing is made on an object which is visually overlapped with the focusing zone corresponding to a selected one of the various focusing zones of the finder.

Another object of the present invention is to provide an eye direction detecting apparatus for a camera for detecting the eye direction of a photographer using a one-dimensional line sensor.

According to the teachings of the present invention, an eye direction detecting apparatus for a camera having a light transferring system for guiding a beam of parallel light rays to an eye of a photographer includes a light receiving system having a light receiving portion on which a first Purkinje image based on specular reflection of a cornea of the eye and reflecting light from a retina of the eye is formed, the light receiving portion generating a light receiving output; and a processing circuit for detecting the eye direction of the eye based on the light receiving output of the light receiving portion.

In embodiments of the present invention, the eye includes a pupil and the pupil has a periphery, the light receiving portion includes a one-dimensional line sensor, the processing circuit establishes a coordinate corresponding to the periphery of the eye by processing output from the one-dimensional line sensor in one slice level, the processing circuit establishes a coordinate corresponding to the first Purkinje image by processing output from the one-dimensional line sensor in another slice level, and the eye direction is detected by calculation of a central coordinate of the first Purkinje image and a central coordinate of the periphery of the pupil.

In certain embodiments of the present invention, the light receiving portion includes a primary line sensor and the processing circuit includes means for separating the output from the one dimensional line sensor into a retina reflecting light corresponding output composition corresponding to a reflecting light from the retina and a first Purkinje image forming reflecting light corresponding output composition corresponding to a reflecting light for forming the first Purkinje image and for finding a gravity position of the separated retina reflecting light corresponding to the composition and the gravity position of first Purkinje image forming reflecting light, thereby to detect the eye direction, respectively.

According to the teachings of the present invention, the light receiving system may include a reimaging lens for reimaging reflecting light for forming the first Purkinje image on the one-dimensional line sensor based on a corneal specular reflection, and the processing circuit may include a correcting means for correcting a decrease of a peripheral portion incident light amount based on the light amount distribution characteristics of the reimaging lens.

In embodiments of the present invention, the position of the first Purkinje image and the position of the pupil may be established by bit inverting the separated retina reflecting light corresponding output composition and the first Purkinje image forming reflecting light corresponding output composition.

According to the teachings of the present invention, an eye direction detecting apparatus of a camera includes a light transferring system for radiating a detecting light in the form of a parallel pencil of rays towards an eye looking into a finder magnifier, and a light receiving system having a light receiving portion for reimaging the detecting light for forming a virtual image on the light receiving portion based on corneal specular reflection of the eye, wherein the finder magnifier is provided at the side of the finder magnifier facing the eye with a coaxis forming optical member for making the optical axis of the light transferring system and the optical axis of the light receiving system coaxial.

In embodiments of the present invention, the light receiving system may include a reducing lens and a reimaging lens disposed between the coaxis forming optical member and the light receiving portion, and the reducing lens may have at least one aspherical surface. The coaxis forming optical member may be a mirror which permits visible light to pass therethrough and which has a reflecting and transmitting characteristic with respect to infrared light. Alternatively, the coaxis forming a optical member may be a prism. In such a case, the prism may have a first transmitting surface facing the eye, a second transmitting surface opposite the first transmitting surface, and a reflecting surface disposed between the first transmitting surface and the second transmitting surface and facing the finder magnifier and, further, wherein first transmitting surface is slightly inclined with respect to the coaxis.

According to the teachings of the present invention, an eye direction detecting optical system includes a viewing area having a plurality of zones to which the eye can be selectively directed, and means for determining to which of the plurality of zones the eye is directed, the means for determining comprising means for compensating for a difference between determined eye direction and actual eye direction. The means for compensating for a difference between determined eye direction and actual eye direction may include a means for compensating for a difference caused by light amount damping. The means for compensating for a difference caused by light amount damping may include means for determining an amount of light amount damping. Such means, may also include means for generating a light amount correcting value based upon the determined amount of light amount damping. Such means may still further include either a read-only memory (ROM) element and/or an electrically erasable programmable read-only memory (EEPROM) element.

In embodiments of the present invention, the eye may have a cornea and a retina, and the means for determining may further include means for directing light towards the eye, and means for generating a light amount distribution including a first Purkinje image composition based on corneal specular reflection and a retinal reflecting composition based on reflecting light from the retina. The means for determining may further include means for separating the first Purkinje image composition and the retinal reflecting composition. The light amount distribution may have a plurality of output levels, and the means for separating may include means for establishing a plurality of zone levels, and means for determining the number of output levels terminating in each of the plurality of zone levels. The means for determining may include a plurality of frequency registers, one frequency register for each zone level. The means for determining may further include means for determining light amount distribution appearance in a predetermined zone.

In embodiments of the present invention, a boundary line may exist between the first Purkinje composition and the retinal reflecting composition, and the means for determining may further include means for establishing an at least one slice level in the vicinity of the boundary line.

In embodiments of the present invention, the means for determining light amount distribution appearance may include at least one frequency register having an output, and the means for establishing an at least one slice level in the vicinity of the boundary line may operate based upon the output of the at least one frequency register.

According to the teachings of the present invention, the light amount distribution has a central or gravity position, and the means for determining may further include means for calculating the gravity position. The means for calculating the gravity position may include means for calculating a first phase difference between the separated first Purkinje image composition and retinal reflecting composition, separating the first Purkinje image composition and the retinal reflecting composition, calculating a second phase difference between the inverted first Purkinje image composition and retinal reflecting composition, and calculating the gravity position based upon the first phase difference and the second phase difference.

According to the teachings of the present invention, an eye direction detecting optical system includes means for directing light rays towards the eye; means for receiving light rays reflected by the eye, the means for receiving generating a light amount distribution; means for compensating for damping of the amount of light received at the means for receiving; means for determining gravity position of the light amount distribution, after compensation for light amount damping; and means for determining eye direction based upon the determined gravity position. The means for compensating may include means for developing a correction factor. The means for compensating may further include means for normalizing the correction factor to develop a correction value. The means for compensating may further include a means for storing the correction value, such as a read-only memory (ROM) or an electrically erasable programmable read-only memory (EEPROM).

A system according to the present invention may further include means for correcting based upon the stored correction value.

In embodiments of the present invention wherein the eye has a cornea and a retina, the means for receiving may generate a light amount distribution based on corneal specular reflection and reflecting light from the retina.

According to the present invention, means for determining gravity position of the light amount distribution may include means for separating distribution effects resulting from corneal specular reflection and distribution effects resulting from reflecting light from the retina. The means for determining gravity position may further include means for establishing a slice level of the light amount distribution.

In embodiments of the present invention, a boundary line may exist between the distribution effects of the corneal specular reflection and the distribution effects of the reflecting light from the retina. In such embodiments, means for establishing a slice level may establish the slice level in the vicinity of the boundary line. The means for establishing a slice level may comprise means for providing a plurality of zone levels, and means for selecting a zone level in which to establish the slice level. In embodiments of the present invention, the light amount distribution may have a varying output frequency and the means for selecting a zone level in which to establish the slice level may select a zone level based on the varying output frequency. The means for selecting a zone level may include at least one frequency register, which at least one frequency register is adapted to provide an output indicative of output frequency with a predetermined zone level. In certain embodiments of the present invention, there may be a plurality of frequency registers, one for each of the zone levels.

According to the teachings of the present invention, an eye direction detecting apparatus includes means for directing light rays towards the eye; includes means for receiving light rays reflected by the eye, the means for receiving generating a light amount distribution having a gravity position; and processing means for calculating the gravity position. In embodiments of the present invention, wherein the eye has a cornea and a retina, the light amount distribution may have a corneal specular reflection component and a retina reflection light component. In embodiments of the present invention, the processing means may include means for determining a first phase difference between the corneal specular reflection and component the said retina reflecting light component. The processing means may further include means for inverting the corneal specular reflection component and the retina reflecting light component. The processing means may further include means for determining a second phase difference between the corneal specular reflection component and the retina reflecting light component. In embodiments of the present invention, the processing means may further include means for calculating the gravity position based on the first phase difference and the second phase difference.

According to the teachings of the present invention, an eye direction detecting apparatus includes a light transferring system having an optical axis; a light receiving system having an optical axis; means for making the axis of the light receiving system and the optical axis of the light receiving system coaxial; and means for preventing refracted light from forming a ghost image within the light receiving system. In embodiments of the present invention, the means for making may include an optical member having at least two transmitting surfaces, each of the at least two transmitting surfaces having an identical angle of inclination with respect to the coaxial axes. In embodiments of the present invention, the light transferring system may include means for emitting light, the light receiving system may include a light sensor, the apparatus may further include means for directing the emitted light into the eye, and light reflected from the eye may form a light amount distribution on the light sensor. In embodiments of the present invention the eye may have a cornea and a retina and the light amount distribution may have a corneal specular reflection component and a retinal reflecting light component.

Any, all, or any components of the systems and/or apparatus of the present invention may be incorporated into a camera. Such a camera may have an auto focusing capability.

A feature of an eye direction detecting apparatus for a camera according to the present invention is that a camera body is provided with a light transferring system for guiding a parallel pencil of rays to an eye of a photographer; a light receiving system having a light for forming a first Purkinje image based on a corneal specular reflection of the eye and a reflecting light from the retina of the eye is present; and a processing circuit for detecting the eye direction of the eye of the photographer based on a light receiving output of the light receiving portion is present.

A further feature of an eye direction detecting apparatus of a camera according to the present invention is that the light receiving portion comprises a one dimensional line sensor, and the processing circuit includes means for separating the output from the primary line sensor into a retina reflecting light corresponding output composition corresponding to a reflecting light from the retina and a first Purkinje image forming reflecting light corresponding output composition corresponding to a reflecting light for forming the first Purkinje image and means for finding gravity position of the separated retina reflecting light corresponding to the composition and the gravity position of a first Purkinje image forming reflecting light, thereby to detect the eye direction, respectively.

BRIEF DESCRIPTION OF THE DRAWINGS

Other objects, advantages, and new features of the invention will become apparent from the following detailed description of the invention when considered in conjunction with the accompanying drawings wherein:

FIGS. 7 through 20 are schematic views for explaining an eye direction detecting optical system for use in an auto optical focus detecting device of a single-lens reflex camera according to the invention of the parent of the present case wherein:

FIG. 7 is a schematic view for explaining the detecting principle of an eye direction detecting optical system according to the invention of the parent of the present case and is a schematic view showing how a light spot is formed when a parallel pencil of rays are projected to a convex mirror;

FIG. 8 is a schematic view showing how a first Purkinje image is formed when a parallel pencil of rays are projected to the cornea of an eye;

FIG. 9 is an enlarged view of an eye for explaining the relation between the first Purkinje image and the center of the pupil;

FIG. 11 is a plan view of a finder of an auto optical focus detecting device;

FIG. 12 is a schematic view showing the relation among an eye direction detecting optical system and a finder magnifying lens used in an auto optical focus detecting device of a single-lens reflex camera according to the invention of the parent of the present case and the user's eye.

FIGS. 13 and 14 are detailed illustrations of an eye direction detecting optical system;

FIG. 15 is an enlarged view of a reimaging lens of FIGS. 13 and 14;

FIG. 16 is a schematic view of the eye direction detecting optical system;

FIG. 17 is a graph of a spherical aberration when a minifying lens of FIGS. 13 and 14 is not an aspherical lens;

FIG. 18 is a graph of a distortion when the spherical aberration of FIG. 17 is present;

FIG. 19 is a graph of a spherical aberration when the minifying lens of FIGS. 13 and 14 is an aspherical lens;

FIG. 20 is a graph of a distortion when the spherical aberration of FIG. 19 is present;

FIGS. 21 through 24 are schematic views for explaining a modified embodiment of the eye direction detecting optical system for use in the auto optical focus detecting device of a single-lens reflex camera according to the present invention, wherein:

FIGS. 21 and 22 are schematic views showing the relation among the reimaging lens and the finder magnifying lens of the eye direction detecting optical system for use in the auto optical focus detecting device of the camera according to the present invention, the user's eye and a one-dimensional line sensor;

FIGS. 23 and 24 are schematic views for explaining the inconvenience when the one-dimensional line sensor is used as a light receiving element of the eye direction detecting optical system;

FIGS. 28 and 29 are illustrations for explaining an image separation processing means;

FIGS. 30, 31(A), 31(B), 31(C), 31(D), 31(E), 31(F), and 32 are graphs for explaining how to find the gravity position of an image separation output distribution;

FIGS. 33 through 37 are illustrations for explaining still another example of an optical system of the eye direction detecting apparatus according to the present invention, wherein;

FIG. 33 is an illustration for showing the constitution of an optical system of the eye direction detecting apparatus;

FIG. 34 is an enlarged view of an important portion of the optical system of the eye direction detecting apparatus shown in FIG. 33;

FIG. 35 is an enlarged view of the reimaging lens shown in FIG. 33;

FIGS. 36 and 37 are illustrations for explaining the optical characteristics of the optical system of the eye direction detecting apparatus shown in FIG. 33;

FIGS. 38 through 40 are illustrations for explaining another example of the optical system shown in FIG. 33, wherein:

FIG. 38 is an optical diagram showing the constitution of an important portion of the optical system of the eye direction detecting apparatus; and FIGS. 39 and 40 are illustrations for explaining the optical characteristics of the optical system shown in FIG. 38.

DETAILED DESCRIPTION OF THE INVENTION

Figure 1:
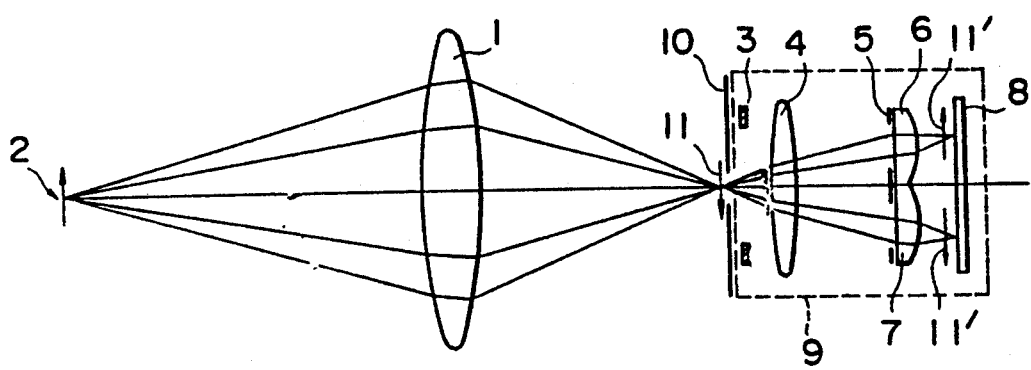
FIG. 1 is a schematic view of a conventional auto optical focus detecting device of a single-lens reflex camera.
Figure 2:
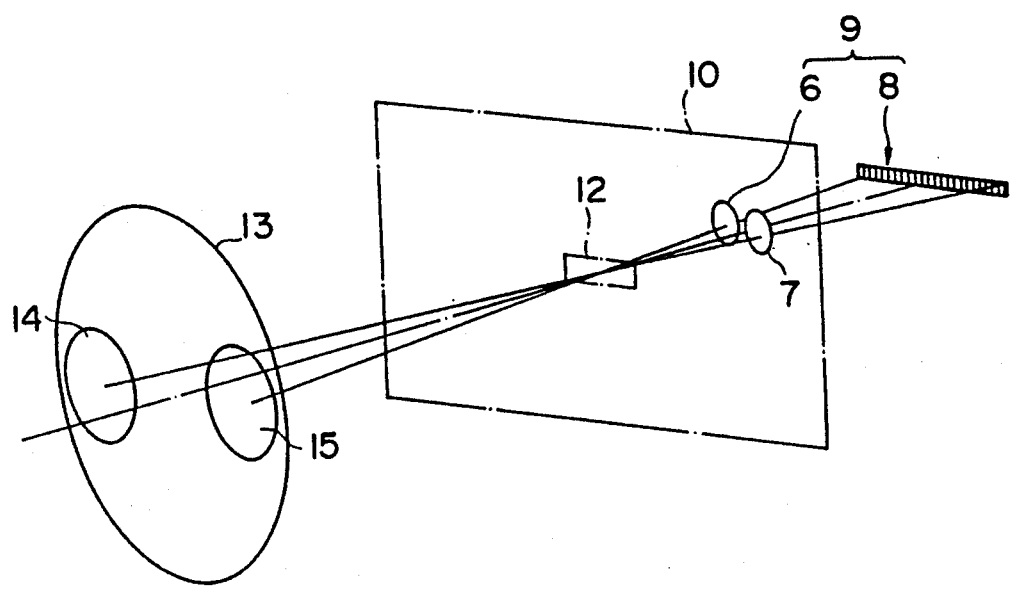
FIG. 2 is a perspective view schematically showing an arrangement of an auto focus optical system of FIG. 1.
Figure 4:
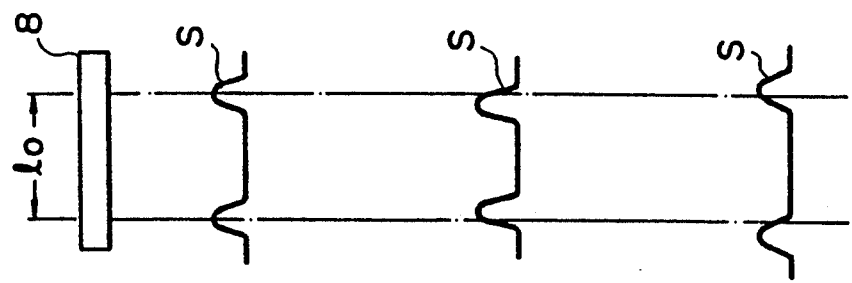
FIG. 4 is a schematic view of a detecting output of a CCD of the auto optical focus detecting device.
Figure 3A:
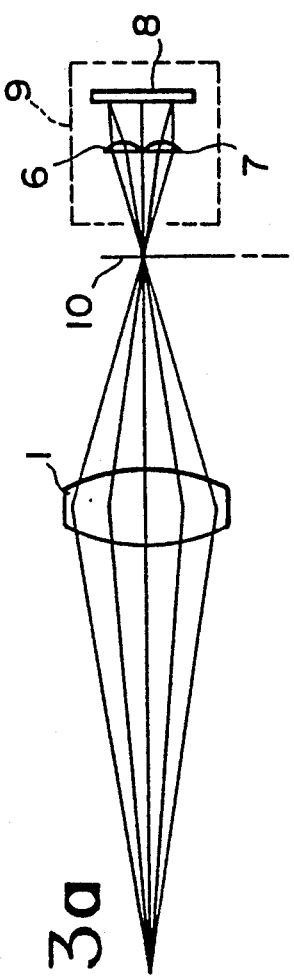
FIGS. 3(A), 3(B) and 3(C) are schematic views for explaining focusing by means of the auto optical focus detecting device.
Figure 3B:
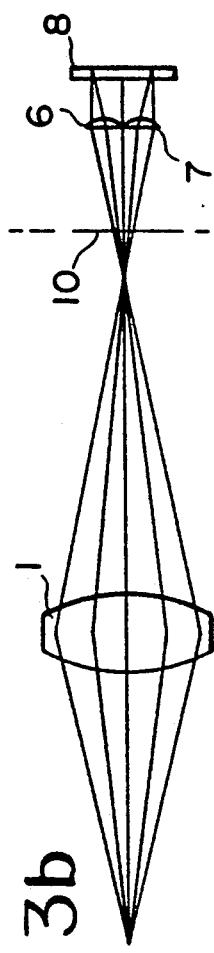
Figure 3C:
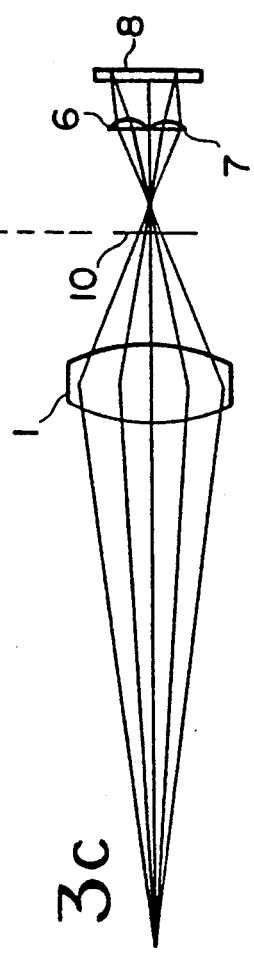
Figure 5:
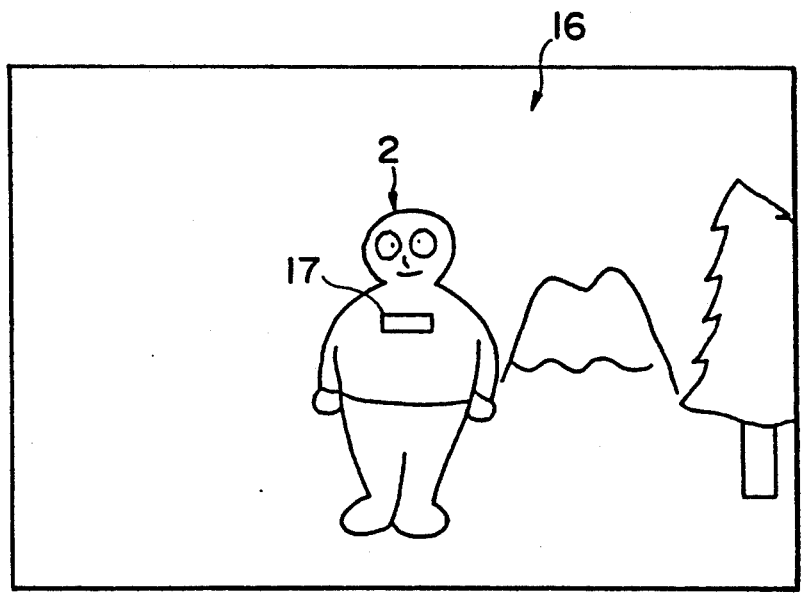
FIG. 5 is a schematic view for explaining an arrangement of a zone to a finder according to a conventional optical focus detecting device.
Figure 6:
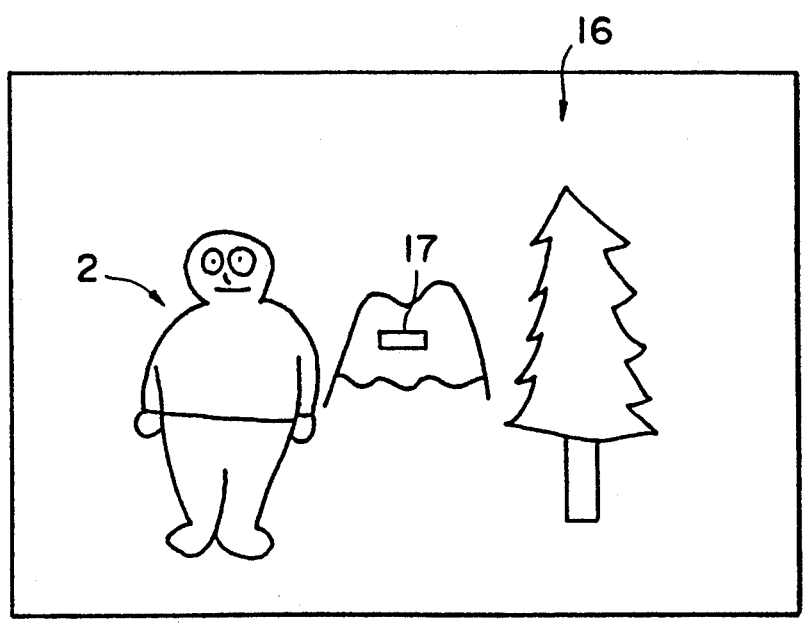
FIG. 6 is a schematic view for explaining the photographing procedure in order to obtain a photograph with a desired subject displaced to right and left areas from the center by using the conventional auto optical focus detecting device.

For clarity and convenience, pertinent sections of the parent application of this application are discussed herein. Also for clarity and convenience, identical reference numerals are used to designate identical or similar elements in both this application and this application's parent.

It should be noted that the expression "eye direction" used in this application means "the direction of a looking or viewing line of an eye", such a line being, of course, an imaginary one. Alternative expressions for this concept are "direction of line of sight" and "the direction towards which an eye is looking". The concept described by all of these expressions should be kept in mind and understood when the short expression "eye direction" is encountered in this application.

As discussed in this application's parent, an eye direction detecting optical system which is used in an auto optical focused detecting device of a single lens reflex camera is described with references to FIGS. 7–20.

A method for detecting an eye direction is described, for example, in an article entitled "Psychological Physic of Vision", written by Mitsuo Ikeda. When it is applied to a camera, only the direction of the user's eye must be detected. In other words, the parallel movement of the user's eye with respect to a view finder of a camera should not be detected. The reasons are as follows. In case the parallel movement of the eye is detected together with the detection of the eye direction, the information on the eye direction is overlapped on that of the angular direction. Therefore, it would be difficult for the camera to sense in which zone the user is looking. If an eye direction detecting optical system which is also able to detect the parallel movement is employed, the relative distance between the optical axis of the finder of the camera and the revolving center of an eye ball of the user must be kept constant. However, in view of the popularity of hand held type cameras, this is practically impossible since the eye is relatively trembled sideward with respect to the finder 16.

An eye direction detecting optical system for detecting the eye direction only in the angular direction is introduced, for example, in "Optical Engineering", of 1974, 7/8 Month, Vol. 23, No. 4, P339–342, Subtitle "Fixation Point Measurement by the Oculometer Technique".

Figure 7:
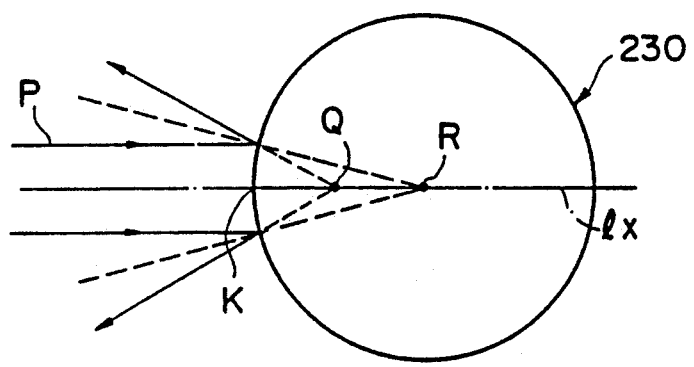
Figure 8:
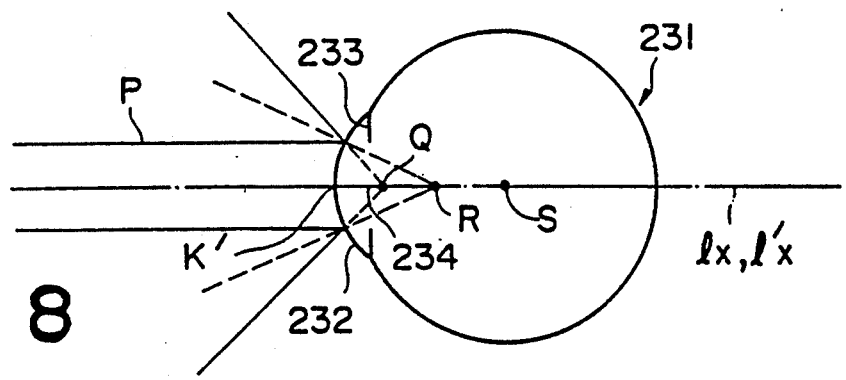

The principle of an eye direction detecting optical system introduced in this article is that, when a parallel $l_x$ is pencil of rays P parallel to an optical axis $l_x$ is radiated to a convex mirror 230, as shown in FIG. 7, an image of a light source located in an optically infinite distance is produced as a light point at a middle point Q between a center R of curvature of the convex mirror 230 and an intersecting point K where the optical axis E x intersects the mirror surface. When the parallel pencil of rays parallel to the optical axis $l_x$ is radiated to a cornea 232 of a human eye 231 as shown in FIG. 8, an image of a light source located in an optically infinite distance is also produced at a light point (this light point is hereinafter referred to as "first Purkinje image PI") at the middle point Q between the center R of curvature of the cornea 230 and a corneal vertex K'. 233 denotes an iris, 234 denotes the center of a pupil, and reference character S denotes the revolving center of an eye ball.

Figure 9:
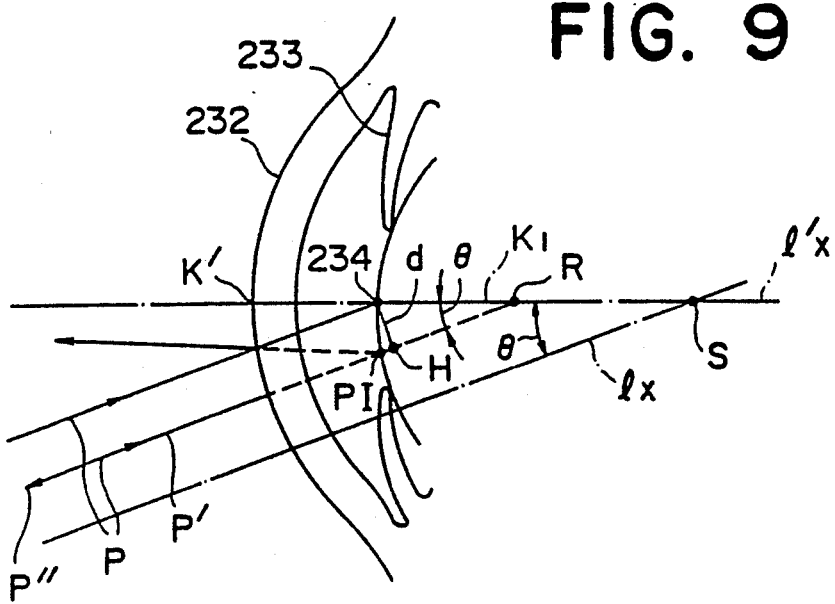

When the optical axis $l_x$ of the bundle of rays P illuminating the cornea 232 is in alignment with the eye direction $l'_x$ showing the direction of the human eye, the center 234 of the pupil, the first Purkinje image PI, the center R of curvature of the cornea 232, and the revolving center S of the eye ball are located on the optical axis $l_x$. Regarding the camera, it is impossible to assume that the revolving center S of the eye ball is located on the optical axis $l_x$ of the view finder. However, it is presumed here that the revolving center S of the eye ball is located on the optical axis $l_x$ and the eye ball is located on the optical axis $l_x$ and the eye ball is sidewardly revolved about the revolving center S. Then, as shown in FIG. 9, a relative gap is produced between the center 234 of the pupil and the first Purkinje image PI. Further, it is presumed that the eye is revolved by an angle $\theta$ with respect to the optical axis length of the $l_x$ and the perpendicular line extending from the center 234 of the pupil to the ray of light which is made incident perpendicularly to the cornea 232 is denoted by d. The following relation can be obtained:

$$d = k_1 \cdot \sin \theta \quad (1)$$

wherein $k_1$ is a distance from the center 234 of the pupil to the center R of curvature of the cornea 232. Although there are individual differences, according to MIL-HDBK-141 "OPTICAL DESIGN" edited by the U.S. Department of Defense, the distance $k_1$ is about 4.5 mm. Reference character H denotes an interesting point where the perpendicular line extending from the center 234 of the pupil to the ray of light P' which is made perpendicularly incident to the cornea 232 intersects the ray of light P'.

As apparent from the above relation (1), since the distance $k_1$ is known, if the length d is found, the revolving angle $\theta$ can be obtained.

In view of the fact that the intersecting point H and the first Purkinje image PI are located on the ray of light P', the parallel pencil of rays P are radiated toward the cornea 232 and if the ray of light P'' reflected and returned in the direction parallel to the incident bundle of rays among the specular reflection from the cornea 232 is detected, and if the relation between the center 234 of the pupil and the first Purkinje image PI is found, the revolving angle $\theta$ of the eye can be obtained.

Figure 10A:
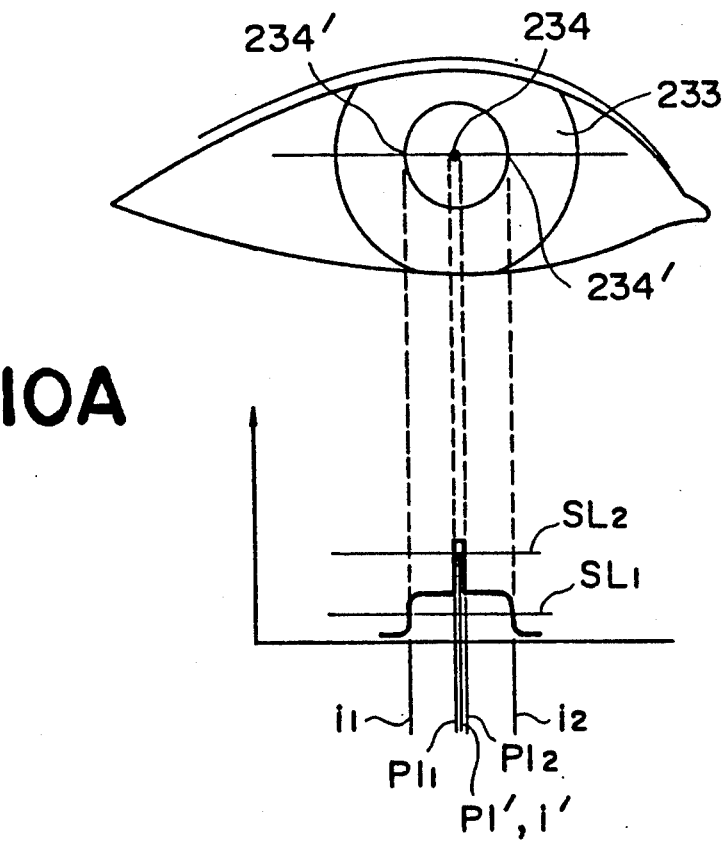
FIGS. 10(A) and 10(B) are schematic views for obtaining the eye direction from the first Purkinje image and the center of the pupil by arithmetic operation.
Figure 10B:
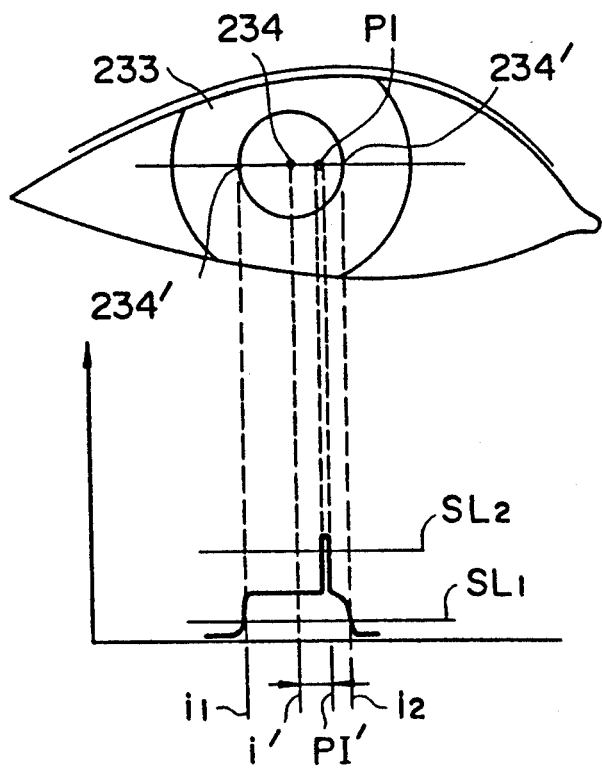

Therefore, assume the parallel pencil of rays P are projected to the eye. If the periphery or boundary 234' of the pupil with the iris appears as a silhouette based on the light reflected by the eye fundus or retina, and the first Purkinje image PI are imaged on the light receiving element such as, for example, the solid photosensitive element as shown in FIGS. 10(A) and 10(B), the output of the received light has a peak at the place corresponding to the first Purkinje image on the light receiving element and the place corresponding the light reflected by the eye fundus becomes a trapezoidal shape. Therefore, the coordinates $i_1$, $i_2$ corresponding to the periphery 234' of the pupil are found by a slice level SL. Then, the coordinates $PI_1$, $PI_2$ corresponding to the first Purkinje image PI are found by a slice level $SL_2$. Then, a difference $d' = PI' - i'$ between the coordinates $i'$ and the coordinates PI' corresponding to the center 234 of the pupil is calculated from the relations (2) and (3) set forth hereunder. If the power of the detecting optical system is denoted by m here, the distance d can be found from the following relation (4):

$$i' = (i_1 + i_2)/2 \quad (2)$$

$$PI' = (PI_1 + PI_2)/2 \quad (3)$$

$$d = d'/m \quad (4)$$

Therefore, if such eye direction detecting optical system is employed, it can automatically determine the zone which is being viewed among the plurality of zones provided by the finder 16.

In the description of the principle, the center of each coordinate is found by arithmetic means. However, in view of the strength of the light received, or luminance thereof, the center of the coordinate may be found by weighted mean.

A specific example of an eye direction detecting optical system which is used in an auto optical focus detecting device of a single-lens reflex camera according to the present invention will now be described.

Figure 12:
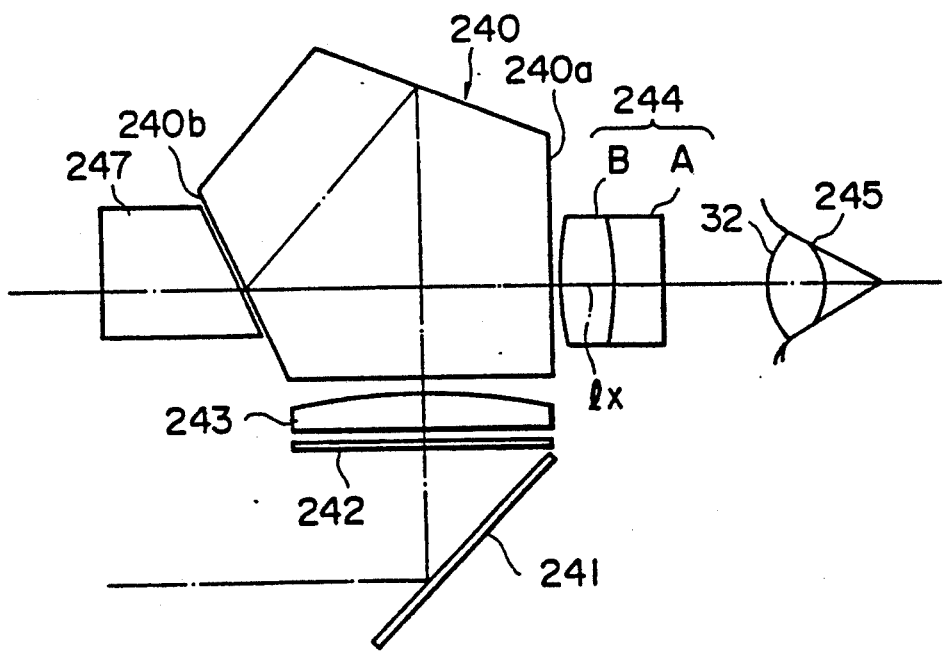

In FIG. 12, 240 denotes a pentagonal prism built in a camera, 241 a quick return mirror, 242 a focusing plate, 243 a condenser lens, 244 a finder magnifying lens, 245 an eye of the user, and lx the optical axis of the aforementioned finder optical system. In this example, the finder magnifying lens 244 comprises magnifying lenses A and B.

The camera is provided with a detecting optical system 246 for detecting the direction of the user's eye looking through the finder at the opposite side of the finder or finder eyepiece element magnifying lens 244 with the pentagonal prism 240 disposed therebetween. In FIG. 12, a framework 247 of the eye direction detecting optical system 246 is shown.

Figure 13:
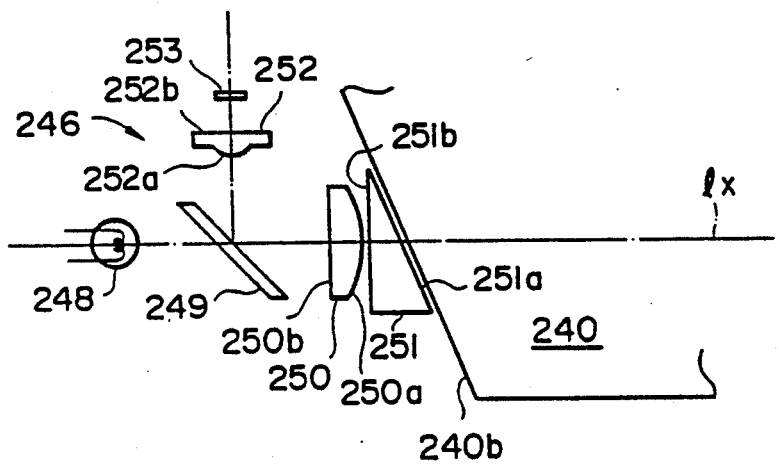
Figure 14:
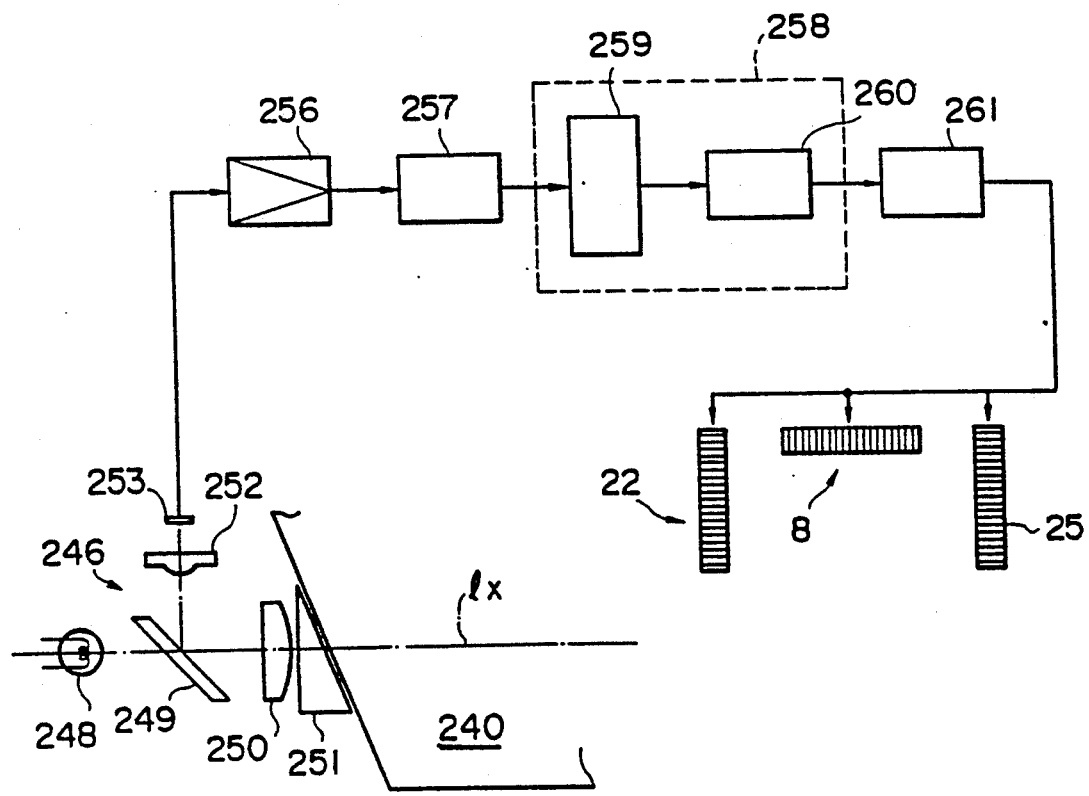

The eye direction detecting optical system 246, as shown in FIGS. 13 and 14, has an infrared light source 248 such as, for example, an infrared light emitting diode for emitting an infrared light. The infrared light is projected to the user's eye 245 as a parallel pencil of rays through a half mirror 249, a minifying lens 250, a compensator prism 251, a pentagonal prism 240, and a finder magnifying lens 244. By this, the first Purkinje image PI is formed based on the specular reflection of the cornea 232. Infrared light is employed in this embodiment so as not to dazzle the user with the illumination of the detecting optical system 246. Similarly, the minilying lens 250 is employed for the reasons that the optical path length of the detecting optical system 246 is made as short as possible so as to be compactly contained in the camera, and that since only the infrared reflecting light parallel to the optical axis lx is employed, the light volume reflected by the eye 245 is considered to be small, and the reflecting light is imaged on as small a dimension as possible on the light receiving surface of the light receiving element as an image receiving element as will be described so as to increase the sensitivity of the light receiving surface of the light receiving element.

Figure 15:
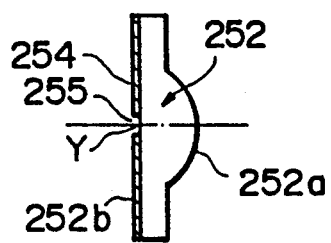

Of the light reflected by the cornea 232 of the eye 245, the bundle of rays parallel to the bundle of incident rays are guided to the half mirror 249 through finder magnifying lens 244, pentagonal prism 240, compensator prism 251, and minifying lens 250, then guided to a reimaging lens 252 by the half mirror 249, and then imaged on a two-dimensional solid photosensitive element 253 (such as, for example, a two-dimensional area CCD), as the image receiving element by the reimaging lens 252. The reimaging lens 252, as shown in FIG. 15, is provided with a mask 254. The mask 254 is formed with an opening 255. The center of the opening 255 is located in the center Y of curvature of the reimaging lens 252. The diameter of the opening 255 is about 0.2 mm in this embodiment.

Figure 16:
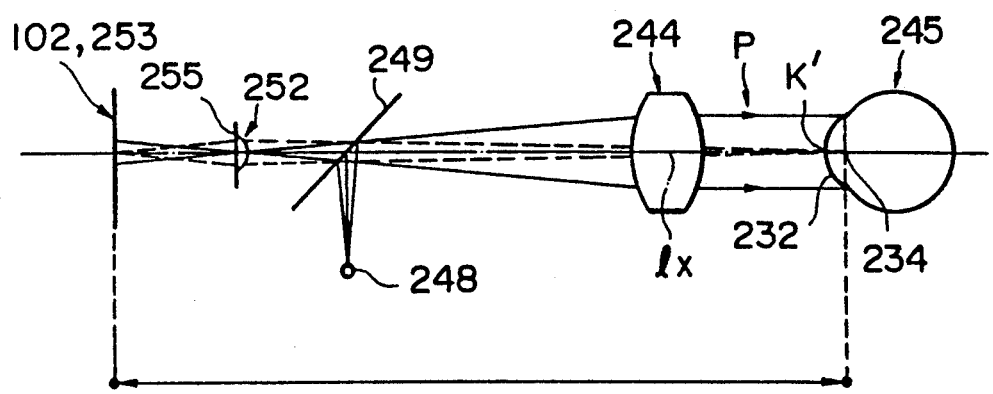

The user's eye 245 is usually placed on an eye point. The solid photosensitive element 253 and the pupil of the user's eye 245, as schematically illustrated in FIG. 16, are in optically conjugate position through finder magnifying lens 244, minilying lens 250, and the reimaging lens 252. On the solid photosensitive element 253, the periphery 234' of the pupil is formed as a silhouette together with the first Purkinje image PI by the light reflected on the eye fundus. Then, the receiving light output of the solid photosensitive element 253, as shown in FIG. 31, is amplified by the amplifier 256, then converted to a digital signal by an analog-digital converter 257, and then temporarily stored in a memory 259 of a microcomputer 258. The memory 259 is memorized with a distance $k_1$ as an information. The information of the distance $k_1$ and the information of the receiving light output are called to an arithmetic circuit 260, then processed based on the relations (1) through (4) to find the revolving angle $\theta$, and then a selected signal meaning which zone has been selected is output to a driver 261 from the revolving angle $\theta$. And, when the CCD of the auto focus optical system corresponding to the selected zone is driven by the driver 261, a distance to the subject to be photographed which is seen overlapped with the zone intended by the user can be automatically found.

Figure 11:
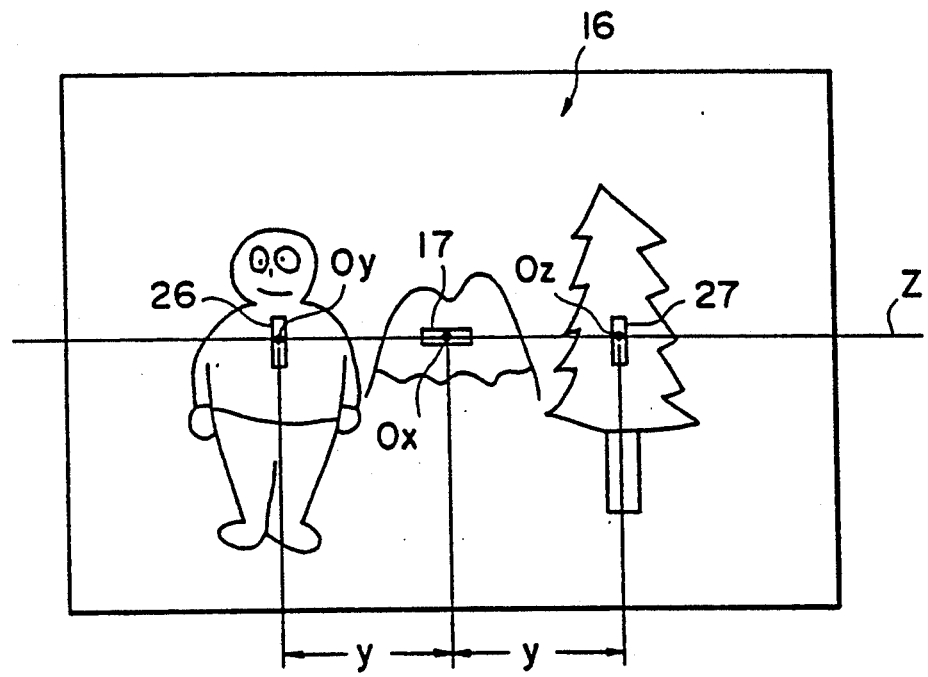

If the distance (the height of an image), as shown in FIG. 11, from the center Ox of the view field (the center of a focusing screen) of the finder 16 to the centers Oy and Oz of the zones at both right and left sides is represented by y, and if a focal distance of the finder magnifying lens 244 is represented by f, the following relation is obtained;

$$y = f \tan \theta \quad (5)$$

If the relation (5) is substituted with the relation (1), the following relation is obtained;

$$y = f d/(k_2' \cos \theta) \quad (6)$$

that is, y is proportional to $d/(k_2'\cos\theta)$. This means that even if the distortion of an image formed on the image receiving element 253 is eliminated, the value of y can not be linearly found from the value of d; in other words, a nonlinearity is present.

In the case of a 35 mm camera, the image height y of a plurality of zones is considered to be about from 6 mm to 9 mm at the largest due to vignetting, etc.

In this embodiment, it is presumed that the eye direction detecting optical system 246 transmits the image of the pupil having the nonlinearity to the image receiving element 253 located behind the system 246 as it is and that the length d detected by the image receiving element 253 is proportional to the image height y. Then, it is merely detected in the longer side by from 0.7 to 1.6% than the actual length d. Therefore, it does not adversely affect the selection of the zone at all. However, from the view point that the accuracy of the eye direction detecting optical system must be improved, it is preferable that the nonlinearity is not present. In such case, it can be corrected by the microcomputer. However, if the distortion is present in the optical system itself, the measurement becomes incorrect. Therefore, the distortion of the optical system must be eliminated as a minimum requirement.

Therefore, in order to make the spherical aberration of the minifying lens 250 small, the plane 250a near the finder magnifying lens 244 is formed in an aspherical plane, and the focal position of the minifying lens 250 is positioned in the center Y of curvature of the reimaging lens 252. In this way, if the minifying lens 250 is formed in an aspherical plane and if the focal point of the minilying lens 250 is positioned in the center Y of curvature of the reimaging lens 252, the opening 255 is brought to be in the center Y of curvature of the reimaging lens 252. Thus, a distortion free optical system can be obtained which is much preferable as an eye direction detecting system.

Next, one example of the designing of such eye direction detecting optical system will be described.

First, a distance from the magnifying lens A to an eye point is set to 14.7 mm, the central thickness of the magnifying lens A is set to 4.98 mm, the radius of curvature of the plane at the eye point side of the magnifying lens A is set to 181,168 mm of a convex, the radius of curvature of the plane at the side facing with the magnifying lens B of the magnifying lens A is set to $-25.500$ mm of a convex, and the refractive index of the magnifying lens A is set to 1.69105. And, a distance between the magnifying lenses A and B is set to 3.01 mm on the optical axis lx. Further, the central thickness of the magnifying lens B is set to 4.10 mm, the radius of curvature of the plane at the side facing with the pentagonal prism 240 of the magnifying lens B is set to $-48,140$ mm of a convex, and the refractive index of the magnifying lens B is set to 1.79175. Further, a distance between the plane 240a of the pentagonal prism 240 and the magnifying lens B is set to 3.21 mm, a length from the plane 240a of the pentagonal prism 240 to the plane 240b is set to 28.00 mm on the optical axis lx, the radius of curvature of each plane 240a, 240b is set to $\infty$ and the refractive index of the pentagonal prisms 240 is set to 1.51260. Next, a space between the plane 251a of the compensator prism 251 and the plane 240b of the pentagonal prism 240 is established to 0.10 mm, and a space between the plane 251b of the compensator prism 251 and the plane 250a of the minifying lens 250 is also established to 0.10 mm. The length of the planes 251b and 251a of the compensator prism 251 is set to 2.00 mm on the optical axis lx, the radius of curvature of each plane 251a, 251b is set to $\infty$, and the refractive index of the compensator prism 251 is set to 1.51260.

The minilying lens 250 is designed as such that the radius of curvature of the plane 250a is 12.690 mm ($k_3 = -3.00$) of a convex, the central thickness is 2.00 mm, and the refractive index is 1.48716. The radius of curvature of the other plane 250b of the minifying lens 250 is set to $-200.000$ mm of a convex, and a space between the reimaging lens 252 and the plane 250b is set to 11.48 mm.

The radius of curvature of the plane 252a of the reimaging lens 252 is set to 1.520 mm of a convex, the radius of curvature of the plane 252b is set to $\infty$, the central thickness of the reimaging lens 252 is set to 1.52 mm, and the refractive, index is set to 1.48716 which is the same as that of the minilying lens 252. Since the mask 254, which has the opening 255 having the diameter of 0.2 mm, is bonded to the plane 252b, the space between the mask 254 and the plane 252b is 0 mm, the thickness of the mask is set to 0.04 mm, and the space between the mask 254 to the light receiving surface of the image receiving element 253 is set to 1.46 mm. The mask 254 and the light receiving surface of the image receiving element 253 is set to $\infty$, and spaces among the respective optical elements are filled with air.

$k_3$ denotes an aspheric spherical coefficient and has the following relation with the sag X:

$$X = h^2 c/(1 + \sqrt{1 - (k_3 + 1)h^2 c^2})$$

wherein h denotes the height from the optical axis lx, and c denotes an inverse number of the radius of curvature of the minifying lens 250.

Figure 17:
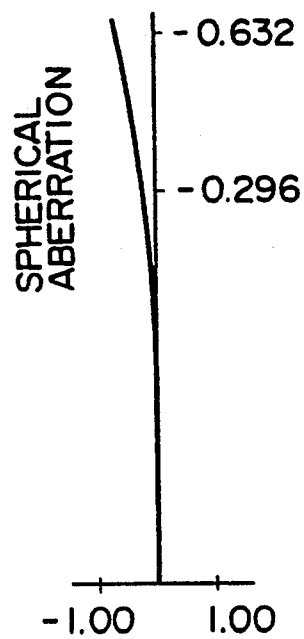
Figure 18:
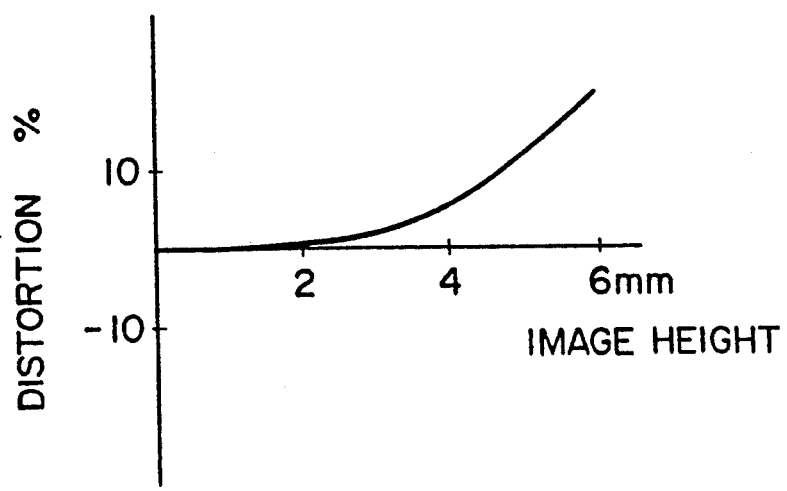
Figure 19:
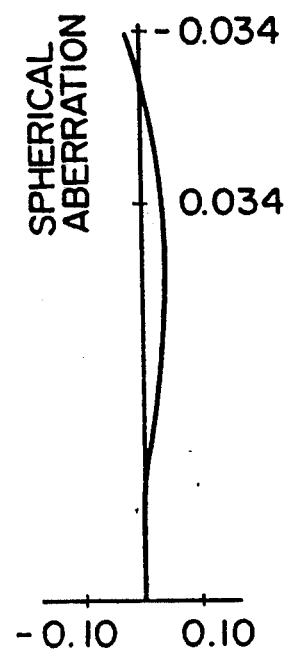
Figure 20:
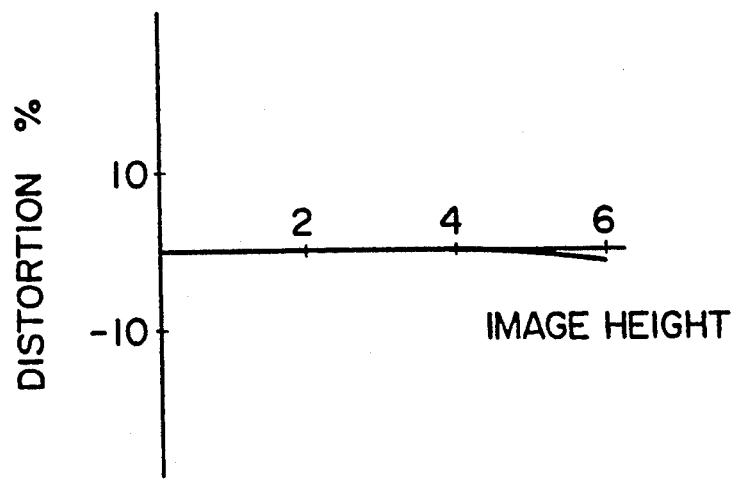

In case the minifying lens 250 is not aspherical, spherical aberration is taken place as shown in FIG. 17, and a distortion is present as shown in FIG. 18. However, if an eye direction detecting optical system which is designed in a way as mentioned above, the spherical aberration is improved as shown in FIG. 19. As a result, the distortion is also improved as shown in FIG. 20.

Although a specific embodiment has been described in the foregoing, it may be designed such that an LED corresponding to each zone 17, 26, 27 is provided within the view field of the finder 16, and the LED corresponding to the selected zone is blinked so as to confirm whether it is the zone intended by the user.

Next, an example of the improvement of an eye direction detecting optical system for use in an auto optical focus detecting device of a single-lens reflex camera according to the present invention will be described.

Figure 23:
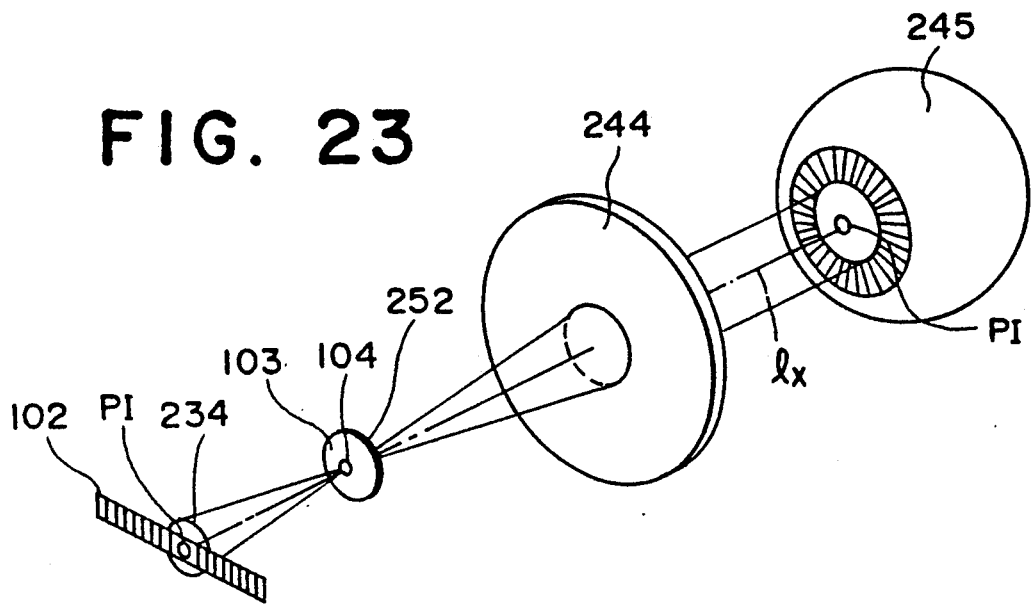
Figure 24:
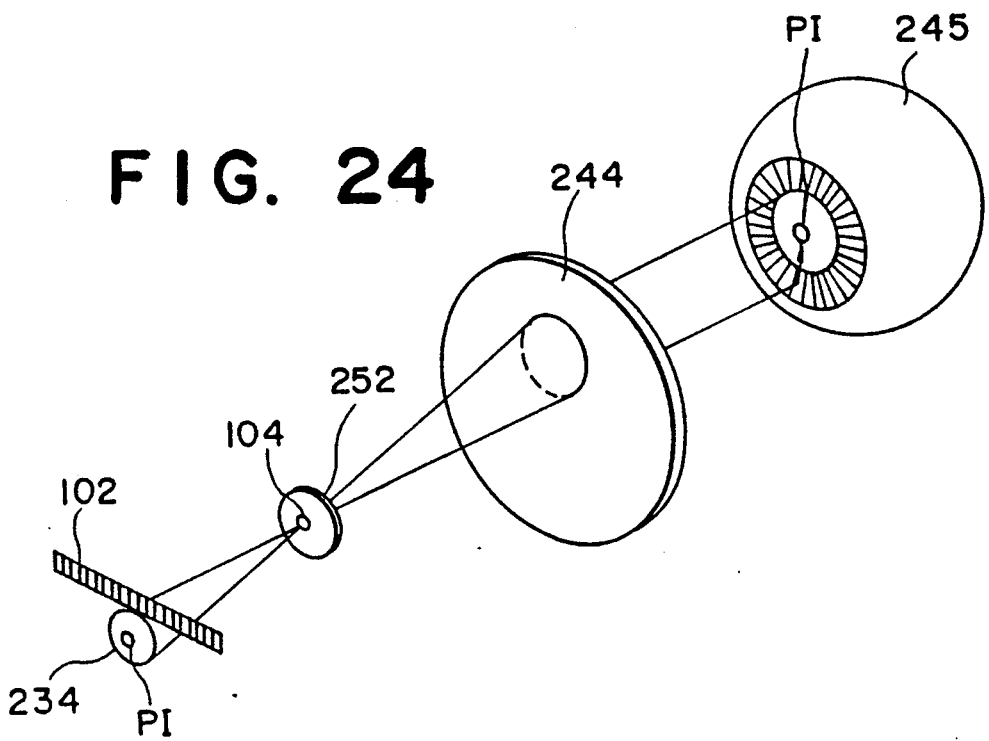

In the aforementioned case, a two-dimensional solid photosensitive element is employed as the image receiving element. However, since the arrangement of the solid photosensitive element is two-dimensional, it is expected that the scan processing time for scanning the solid photosensitive element takes a long time. In addition, the cost becomes high. In one with a plurality of zones 17, 26 and 27 linearly arranged as shown by an arrow Z in FIG. 11, it is conceivable that a one-dimensional line sensor can be employed in which the photoelectronic element is disposed in the direction corresponding to the direction in which the zones 17, 26 and 27 are arranged. However, if such a one-dimensional line sensor is employed, the following problems occur. FIGS. 23 and 24 are illustrations for explaining these problems. In FIG. 24, 244 denotes a finder magnifying lens, 252 a reimaging lens, and 102 a one-dimensional line sensor as the image receiving element. As shown in FIG. 23, when the optical axis lx of the eye direction detecting optical system 246, i.e., the optical axis lx of the finder magnifying lens 244 and the eye direction axis l'x are in alignment, the pupil image 234a as the silhouette (periphery) of the pupil and the first Purkinje image PI are formed on the one-dimensional line sensor 102. Therefore, an eye direction detection can be carried out normally. However, when the human eye 245 is moved in the vertical direction with respect to the camera body, as shown in FIG. 24, the pupil image 234a as the silhouette and the first Purkinje image PI are out of the one-dimensional line sensor 102. Therefore, the eye direction detection is impossible to carry out normally and is thus inconvenient.

Figure 21:
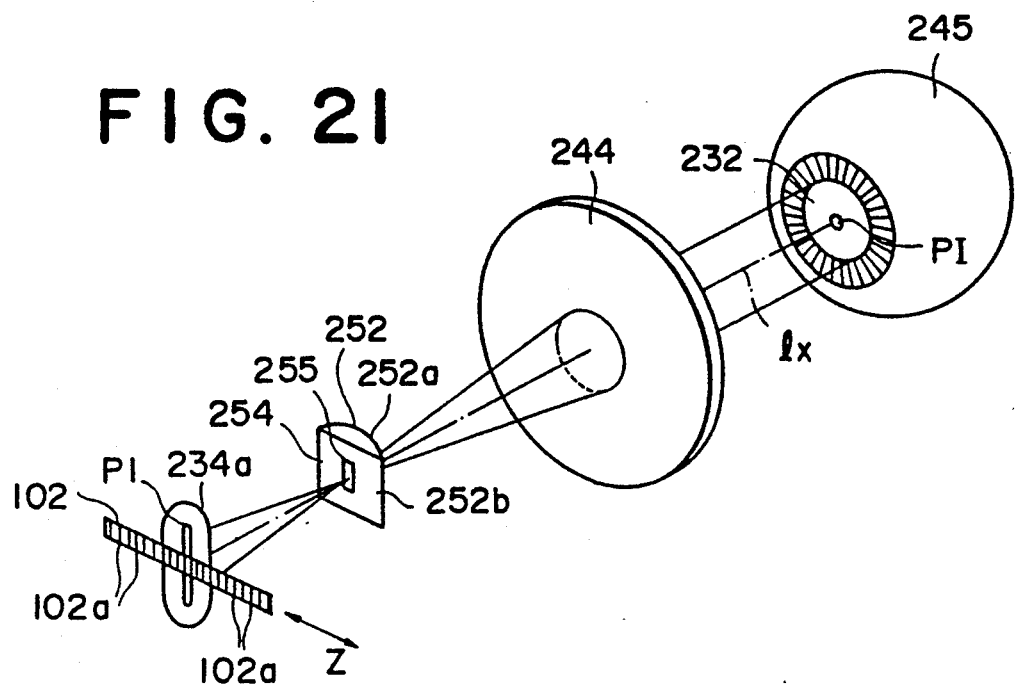
Figure 22:
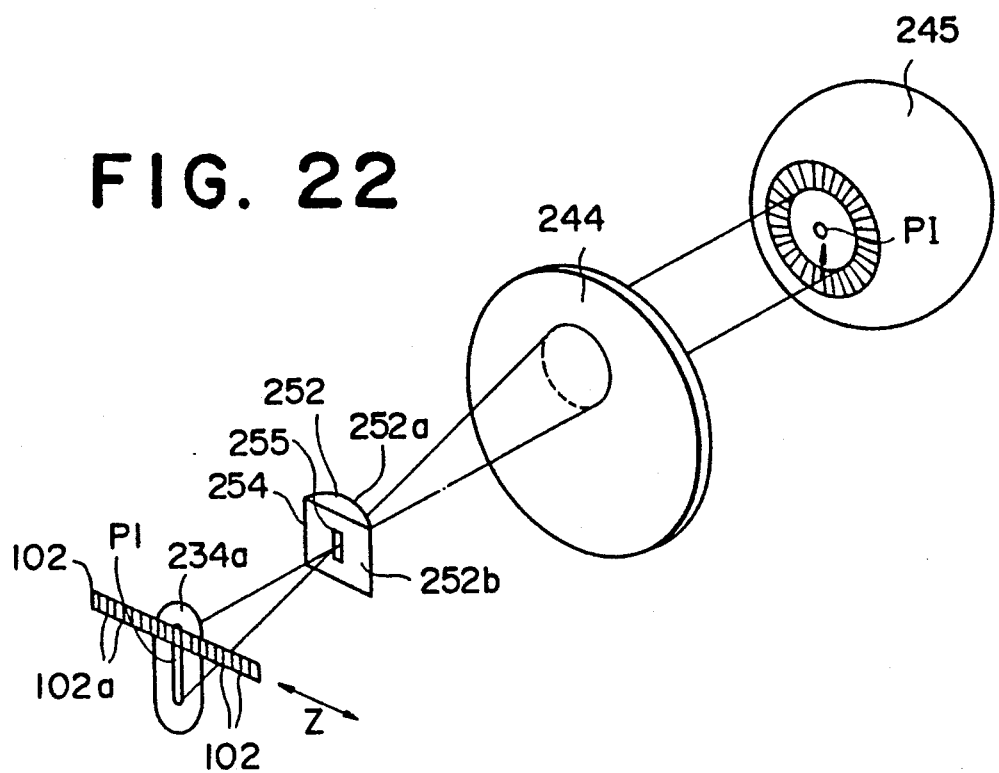

FIGS. 21 and 22 are illustrations for explaining the constitution for avoiding the inconvenience when the one-dimensional line sensor is employed.

In this one-dimensional line sensor 102, as shown in FIGS. 21 and 22, the photoelectronic elements 102 are arranged in a direction corresponding to the direction Z wherein a plurality of zones are arranged. An aramorphic device individual cylindrical lens is employed here as the reimaging lens 252. As shown in FIGS. 21 and 22, a mask 254 is provided to the plain face side of the cylindrical lens. The mask 254 is provided with an opening 255. The center of the opening 255 is located in the center Y of curvature of the reimaging lens 252. The opening 255 is, in this illustration, a rectangular slit. The extending direction of the slit 255 is perpendicular to the arranging direction of the photoelectronic elements of the one-dimensional line sensor 102. The reimaging lens 252 has a spherical surface disposed at the side of the finder magnifying lens 244.

The user's eye 245 is usually placed on the eye point, and the one-dimensional line sensor 102 and the pupil of the user's eye, as schematically illustrated in FIG. 16, are in optically conjugate relation with each other through finder magnifying lens 244, minifying lens 250 and reimaging lens 252. Therefore, the one-dimensional line sensor 102 is formed with the pupil image 234a as the silhouette due to the light reflected by the eye fundus together with the first Purkinje image PI. The reimaging lens 252 is the cylindrical lens and is disposed as such that a vertically elongated first Purkinje image PI and pupil image 234a as the silhouette are formed in the direction perpendicular to the arranging direction of the one-dimensional line sensor 102 on a plane including the one-dimensional line sensor 102. Therefore, even if the eye 245 is moved in the vertical direction with respect to the camera body A₁ as shown in FIG. 22, at least one portion of the respective images PI and 234a are formed on the one-dimensional line sensor 102. Further, since the opening 255 of the mask 254 is also an elongated slit extending in the direction perpendicular to the arranging direction of the photoelectronic elements 102a of the one-dimensional line sensor 102, the pupil image 234a and first Purkinje image PI formed on the plane including the one-dimensional line sensor 102 become longer in the vertical direction, perpendicular to the arranging direction. Therefore, the eye direction detection can be carried out reliably. Therefore, if the receiving light output of each photoelectronic element 102a of the one-dimensional line sensor 102 is amplified by the amplifier 256 and converted to a digital signal by the analog-digital converter 257 to be subjected to a predetermined processing, the eye direction can be detected.

In the aforementioned embodiment, although a cylindrical lens is employed as the reimaging lens 252, a toric lens may be employed.

Another example of a processing circuit of an eye direction detecting apparatus 246 will now be described.

In view of the facts that an optical system of the eye direction detecting apparatus 246 is built in a camera body and that cost increases are to be avoided as much as possible, it is desirable that the optical system be as simple as possible and, reimaging lens 252 is preferably a single lens.

Figure 25:
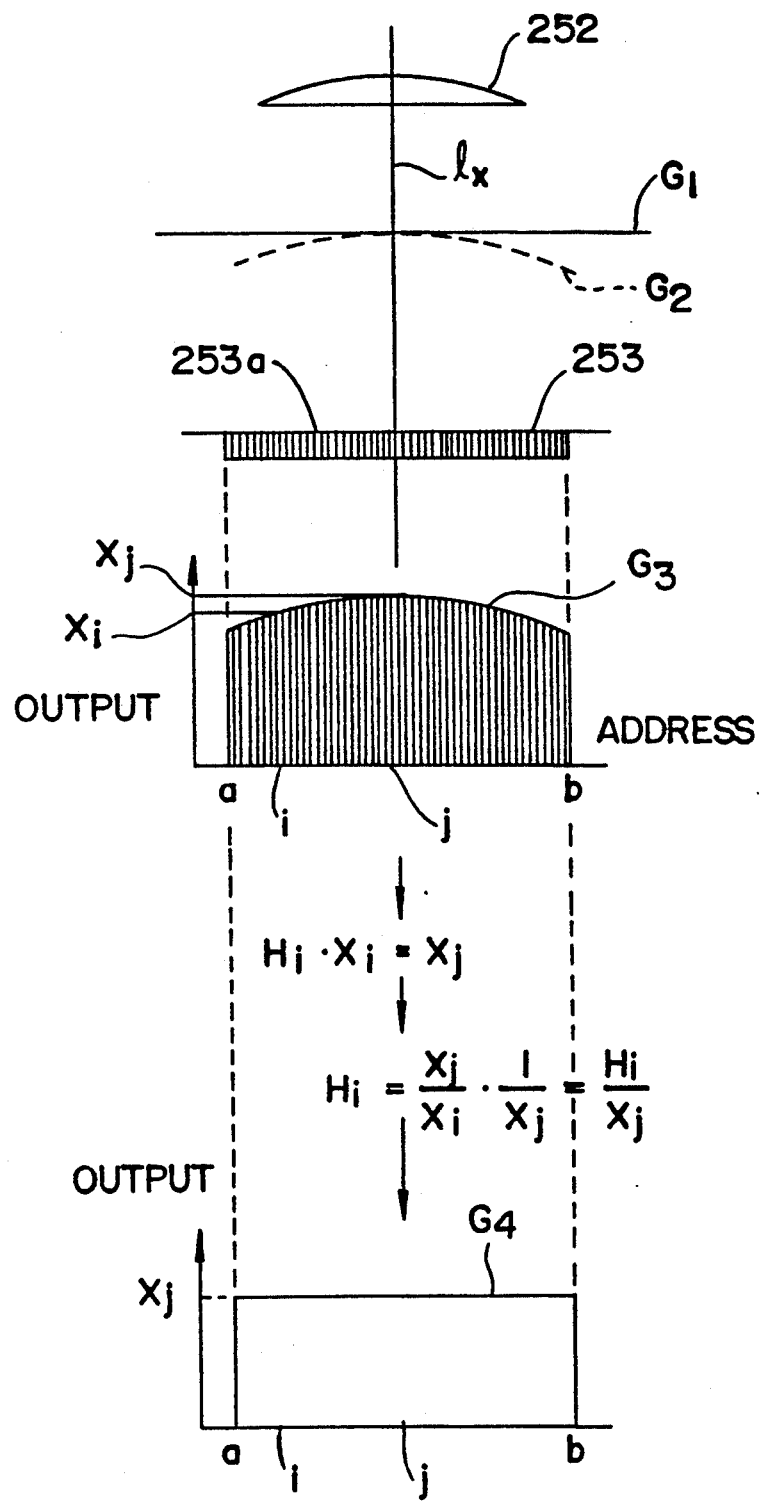
FIG. 25 is an illustration for explaining a correction processing means for correcting the light amount damping at the peripheral portion of the reimaging lens.

However, in the event that such a reimaging lens 252 is used, if light of a uniform light amount distribution is made incident on the reimaging lens 252, the amount of the light imaged on the light receiving surface of a primary line sensor 253 is damped at the peripheral portion as schematically shown in FIG. 25. In FIG. 25, the two-dotted chain line G₁ shows the light amount distribution when the light amount is not damped, the broken line G₂ shows the light amount distribution when the light amount is damped, and l$_x$ shows the optical axis of the optical system of the eye direction detecting apparatus 246 as described.

Where such light amount damping is present, if the gravity position of the light amount distribution is found based on the output of the one-dimensional line sensor 253, there is a risk that such found gravity position is displaced from the actual gravity position and, therefore, if the eye direction is established through calculation using such found gravity position, an error will occur between the actual eye direction and such obtained eye direction.

In case the angle of the eye direction which is to be distinguished is large, the error based on the light amount damping is allowable. However, the error based on the light amount damping cannot be disregarded as the angle of the eye direction, which is to be distinguished, becomes smaller. Any error based on the light amount damping is preferably removed, if possible, in order to correctly detect the eye direction through calculation.

To this end, in the processing circuit, there is provided means for finding the light amount damping beforehand and storing a light amount correcting value in a read-only memory or ROM, which will be described.

That is, the output distribution of the one-dimensional line sensor 253 corresponding to that of the light amount damping becomes something like that shown by reference $G_3$ of FIG. 25. In the figure, reference character i denotes an $i^{th}$ photoelectric element 253a, j denotes a $j^{th}$ photoelectric element 253a, $x_i$ denotes the output of an $i^{th}$ photoelectric element 253a, and $x_j$ denotes the output of a $j^{th}$ photoelectric element 253a. Presume that the $j^{th}$ photoelectric element 253a is located on the optical axis $l_x$. In other words, presume that the $j^{th}$ photoelectric element 253a is a central address between a-address and b-address. In this case, it can be anticipated that the output of the $j^{th}$ photoelectric element 253a is the largest.

Therefore, the various output from the a-address photoelectric element 253a to the b-address photoelectric element 253a are found and the correction factor $H_i$ is found.

The following relational expression is obtained among the correction factor $H_i$, the output $X_i$ and the output $X_j$.

$$H_i X_i = X_j \tag{5}$$

Figure 26:
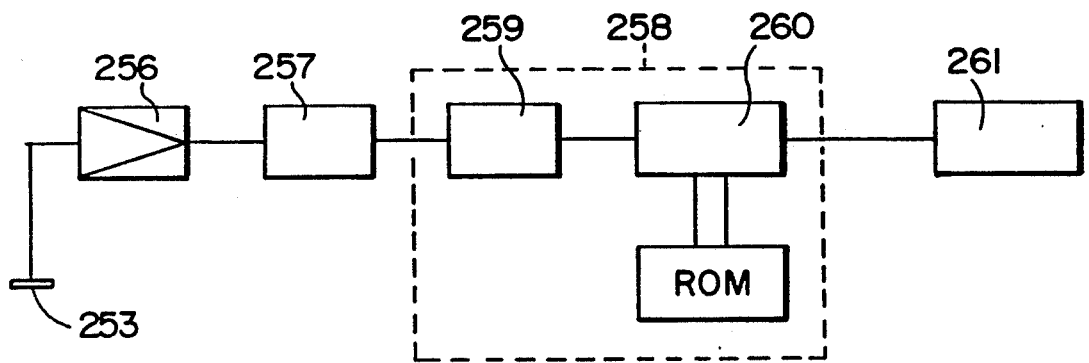
FIG. 26 is a block diagram of a processing circuit having the correction processing means.

In order to normalize the correction factor $H_i$, the correction factor $H_i$ is divided by $X_j$ to find a correction value $H_i'$ and the correction value $H_i$ is stored in the ROM of the processing circuit shown in FIG. 26.

$$H_i' = H_i/H_j \tag{6}$$

If such normalized correction value $H_i'$ is corrected by multiplying it with the output of each address (from a-address to b-address) actually obtained, the output distribution corresponding to the damped light amount distribution is corrected as shown by reference character $G_4$. In other words, there can be obtained a uniform output distribution $G_4$, in which the light amount damping based on the affection of the peripheral portion of the imaging lens 252 with respect to a uniform light is compensated for.

Furthermore, if a correction value based on the light amount distribution obtained when a parallel uniform light is made incident from the finder magnifier 244 is stored for use in a writable and rewritable EEPROM, there can be effected the correction including the error caused by the light amount distribution in the state where the optical elements other than the reimaging lens 252 of the optical system are included, as well as the irregularity of sensitivity of the various photoelectric elements 253a of the primary line sensor 253 itself. Therefore, if such correction is performed, the specification regarding the optical characteristic of the one dimensional line sensor 253 itself can be loosened, and a cost reduction based on the improvement of the yield of production can be obtained.

In order to find a gravity position of the light amount distribution for forming the first Purkinje image PI based on the corneal specular reflection and a light amount distribution gravity position of a reflecting light from the retina respectively, the output of the primary line sensor 253 must be separated into a retina reflecting light corresponding output composition which corresponds to the retinal reflecting light and a first Purkinje image forming reflecting light corresponding output composition which corresponds to the first Purkinje image PI.

Figure 27:
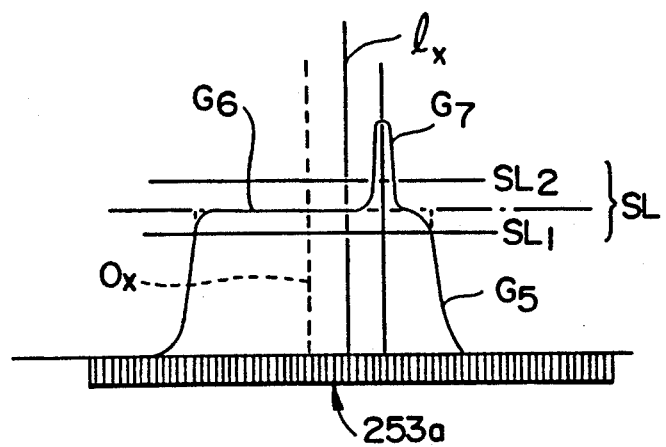
FIG. 27 is a schematic view showing a relation between an actually obtained light amount distribution and the primary line sensor.

That is, the actual light amount distribution becomes something like that shown by the solid line $G_5$ of FIG. 27. Therefore, if the processing is carried out without being separated into the retina reflecting light corresponding output composition $G_6$ and the first Purkinje image forming reflecting light corresponding output composition $G_7$, a gravity position (coordinate or address) including both of them can be found, but the center 234 of the pupil and the center of the first Purkinje image PI cannot be found.

In such a case, in order to separate the retina reflecting light corresponding output composition $G_6$ and the first Purkinje image forming reflection light corresponding output composition $G_7$ as correctly as possible, the slice level SL must be established in the vicinity of the boundary line. To this end, a plurality of zone levels ZN are provided and the output frequency of the photoelectric element 253a is checked.

In this embodiment, 8 pieces of the zone level ZN are provided as shown in FIG. 28. The 8 pieces of the zone level ZN are denoted by reference characters $ZN_1$ through $ZN_8$.

And, in order to check the output frequency of the photoelectric converting element 253a, 8 pieces of appearance frequency register $R_1$ through $R_8$ are provided such a manner so as to correspond with the 8 pieces of zone level $ZN_1$ through $ZN_8$. The bit number of the appearance frequency registers $R_1$ through $R_8$ is 8. And, the output of each photoelectric element 253a from the a-address to the b-address is successively input into the appearance frequency registers $R_1$ through $R_8$. For example, since the output of the a-address is "0" the contents of all appearance frequency register are "0". If the output of the photoelectric converting element 253a of j-address is an output corresponding to "$2^{22}$", the content of the appearance frequency register $R_2$ becomes "00000010" and the contents of the remaining frequency registers are "0". For example, if the output of the photoelectric element 253a of the i+1-address is larger by a portion corresponding to 1 bit than the output "$2^{22}$" of the photoelectric converting element 253a of the i-address, the content of the appearance frequency register $R_3$ becomes "10000010".

Therefore, by paying attention to the high-order 3 bits of the appearance frequency registers $R_1$ through $R_8$, a "+1" is output form the appearance frequency registers $R_1$through $R_8$ when the data of the content of the high-order 3 bits include at least one "1". And, the output of the photoelectric element 253a of each address (i=a through b) is input, and the output of each appearance frequency register $R_1$ through $R_8$ is incrementally counted every time the content of the high-order 3 bits includes at least one "1". When the content of the high-order 3 bits does not include a "1" it is not incrementally counted- In this way, if the appearance frequency registers $R_1$ through $R_8$ are incrementally counted every time the photoelectric element 253a of each address is output, in the case of the output distribution schematically shown, since the number of the photoelectric elements 253a having the output level somewhere between the zone level $ZN_2$ and the zone level $ZN_3$is the largest, the increment count number of the appearance frequency register $R_3$ is expected to become the largest.

Therefore, regarding the output distribution of the photoelectric elements 253a of all addresses, it is judged whether or not the increment count number of the appearance frequency registers $R_1$ through $R_8$ becomes the largest after the increment count. And, the zone level ZN corresponding to the appearance frequency registers $R_1$ through $R_8$ where the increment count number becomes the largest is established as the slice level S1. If this slice level is used, the retina reflecting light corresponding output composition $G_6$ and the first Purkinje image forming reflecting light output composition $G_7$ can be separated.

The width of the zone level $ZN_1$ through $ZN_8$ is established corresponding to the nozzle based on the reflection from the retina, and the composition of this nozzle level can be removed through a low pass filter. However, it can also be removed by means of software processing in which the zone levels $ZN_1$ through $ZN_8$ are overlapped.

Figure 29:
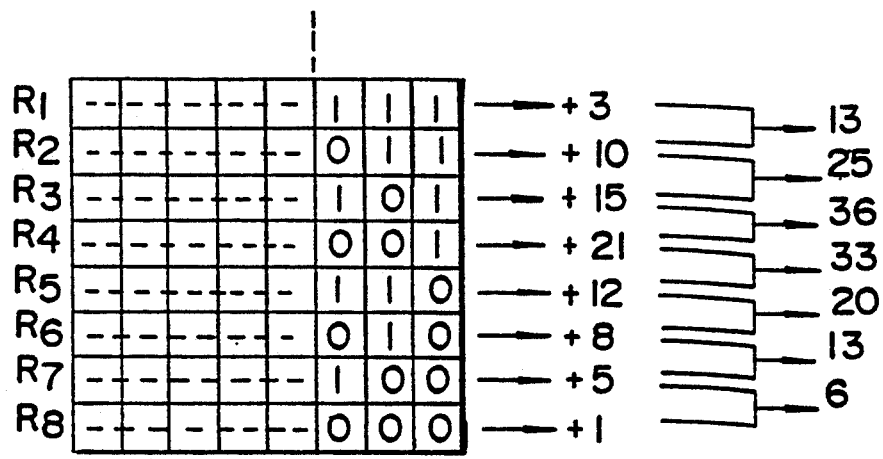

For example, as shown in FIG. 29, the sum of the increment count number of the adjacent appearance frequency registers $R_1$ through $R_8$ are obtained, and the appearance frequency register, in which the sum thereof is the largest, is judged. In the example shown in FIG. 29, since the sum of the appearance frequency register $R_3$ and the appearance frequency register $R_4$ is the largest, it is judged that the increment count number of the appearance frequency register $R_4$ is the largest.

Since the intermediate level appears most frequently among the retina reflecting light corresponding output composition $G_6$, regarding the establishment of the slice level SL, the appearance frequency registers $R_1$ and $R_8$ are not taken into consideration from the beginning.

In this way, the zone level $ZN_4$ corresponding to the appearance frequency register $R_4$ can be found. Herein, it is decided beforehand that it refers to the first Purkinje image forming reflecting light corresponding output composition $G_7$ when the content of the appearance frequency register $R_4$ is "00000001" or more, and that it refers to the retina reflecting light corresponding output composition $G_6$ when the content of the appearance frequency register $R_4$ is "00000110" or less.

Due to the foregoing arrangement, the slice levels $SL_1$ and $SL_2$ as shown in FIG. 27 can be established in the vicinity of the boundary line between the retina reflecting light corresponding output composition $G_6$ and the first Purkinje image forming reflecting light corresponding output composition $G_7$ based on the content of the appearance frequency register $R_4$.

Figure 30:
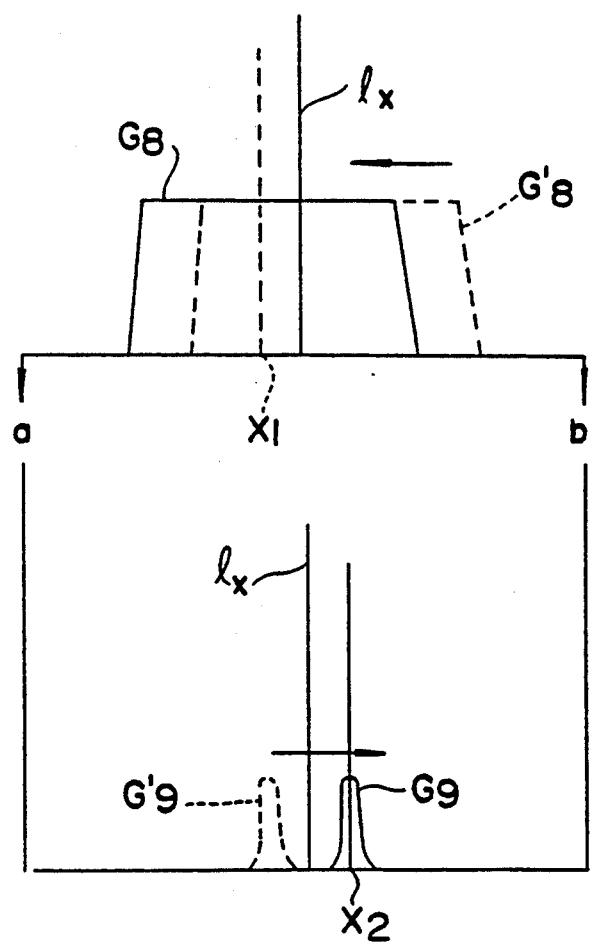
Figure 3I:
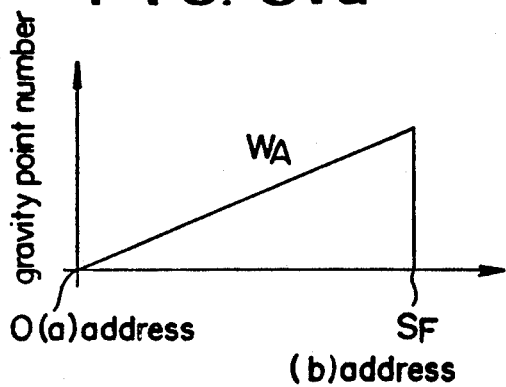
Figure 3I:
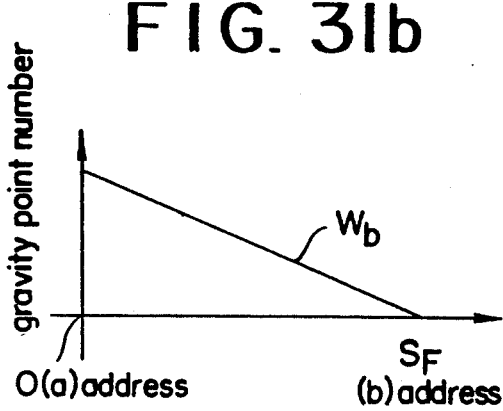
Figure 3I:
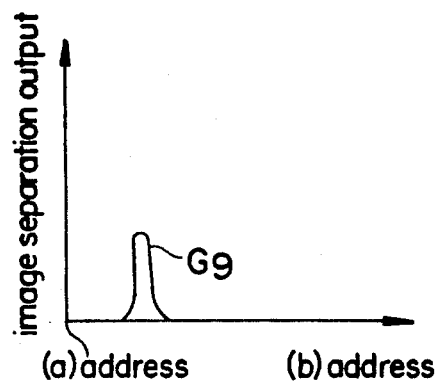
Figure 3I:
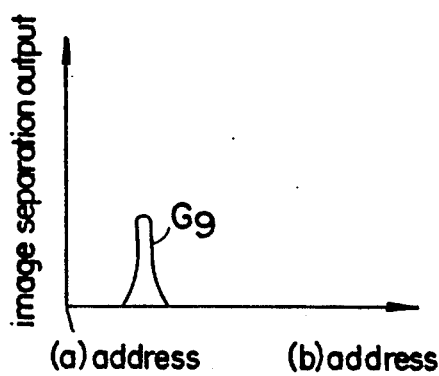
Figure 3I:
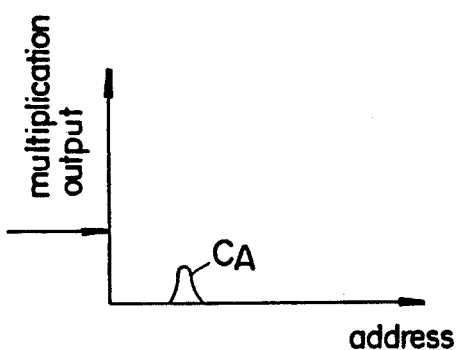
Figure 3I:
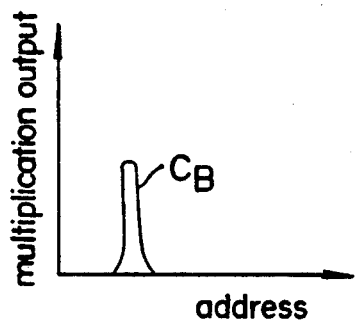

In this way, when the slice levels $SL_1$ and $SL_2$ are established and the output composition corresponding to the light amount distribution characteristic as shown in FIG. 27 is sliced to perform the image separation processing, a separation output as shown in FIG. 30 can be obtained. In FIG. 30 the solid line $G_8$ shows the retina reflecting light corresponding separation output, whereas the solid line $G_9$ shows the first Purkinje image forming reflecting light corresponding separation output. In this embodiment, the configuration of the retina reflecting light corresponding separation output $G_8$ is trapezoid because the aforementioned correction processing has been performed before the output of the one dimensional line sensor 253 is separated into the retina reflecting light corresponding separation output $G_8$ and the first Purkinje image forming reflecting light corresponding separation output $G_9$. Therefore, if the gravity position of the retina reflecting light corresponding separation output $G_8$ is represented by $X_1$ and if the gravity position of the first Purkinje image forming reflecting light corresponding separation output $G_9$ is represented by $X_2$, the distance $d''$ from the center 234 of the pupil to the first Purkinje image can be found from the relation $d''=X_2-X_1$.

As a calculation algorithm for finding the gravity position, one, in which the output of PSD (position sensor diode) is realized by a software calculation, is used. That is, as shown in FIGS. 31(a) and 31(b), the convolution of the image separation output corresponding to the heavy worth functions $W_A$ and $W_B$ is obtained and, thereafter, integrated. For example, the convolution of the image separation output $G_9$ and the heavy worth functions $W_A$, $W_B$ as shown in FIGS. 31(c) and 31(d) is taken to obtain the multiplication outputs $C_A$ and $C_B$. Then, the multiplication outputs $C_A$ and $C_B$ are integrated to obtain the integration values $S_A$ and $S_B$.

Then, the gravity position X can be obtained from the following relation;

$$X = S_F * \{(S_A - S_B)/(S_A + S_B) + 1\} \times \tfrac{1}{2}$$

wherein $S_F$ is the distance from the origin O.

In this method, the multiplication of every bit is required in order to take the convolution. In recent time, since microcomputers having a multiplying function are widely used, the gravity position can be obtained by this method.

However, if this gravity position X is to be found by software, there is an accompanying disadvantage in that it takes quite a bit of time for calculation.

Therefore, a processing means which can calculate the gravity position X in a comparatively short time is employed in this embodiment.

The obtained separation outputs $G_8$ and $G_9$ are bit inverted with respect to the position coordinates to produce the inverse separation outputs $G_8'$ and $G_9'$ as shown in FIG. 30.

According to this method, by calculating the phase difference between the separation outputs $G_8$ and $G_9$ before inverse and the separation outputs $G_8'$ and $G_9'$ after inverse, the gravity position can be obtained with generally the same degree of accuracy as that mentioned above. This phase difference can be found by a calculating method similar to the function system calculation of a phase difference detecting method which is used in a single-lens reflex camera having an auto-focus optical system known per se. In this calculating method, it has been known that there can be obtained an accuracy in such degree as one divided by a figure of several times of ten through one divided by several hundreds of a resolving power of a picture element of a sensor by means of interpolating calculation.

As opposed to a case where an entirely unexpected object is taken, in the case of this eye direction detecting apparatus 246, the pattern which will be obtained can be anticipated. When the reflecting light from the retina and the reflecting light forming the first Purkinje image PI are formed into a spot image on the one dimensional line sensor 253, symmetrical separation outputs $G_8'$ and $G_9'$ can be obtained. Therefore, as shown for example in FIG. 32, if the separation output $G_8'$ is a simple pattern, the center $O_E$ of the rising position coordinate and the falling position coordinate can be anticipated to be generally the gravity position. Therefore, when the phase difference is to be detected, if a calculation is made only with respect to before and after the center $O_E$, the time for calculation can be shortened.

To be more concrete, the output of the primary sensor 253 is represented by (a). Herein, n denotes the address of the photoelectric element 253a of the primary line sensor. By paying attention to the n− and n+1 addresses, the differential output E(n) can be obtained from the following equation;

$$E(n) = S(n+1) - S(n)$$

Figure 32:
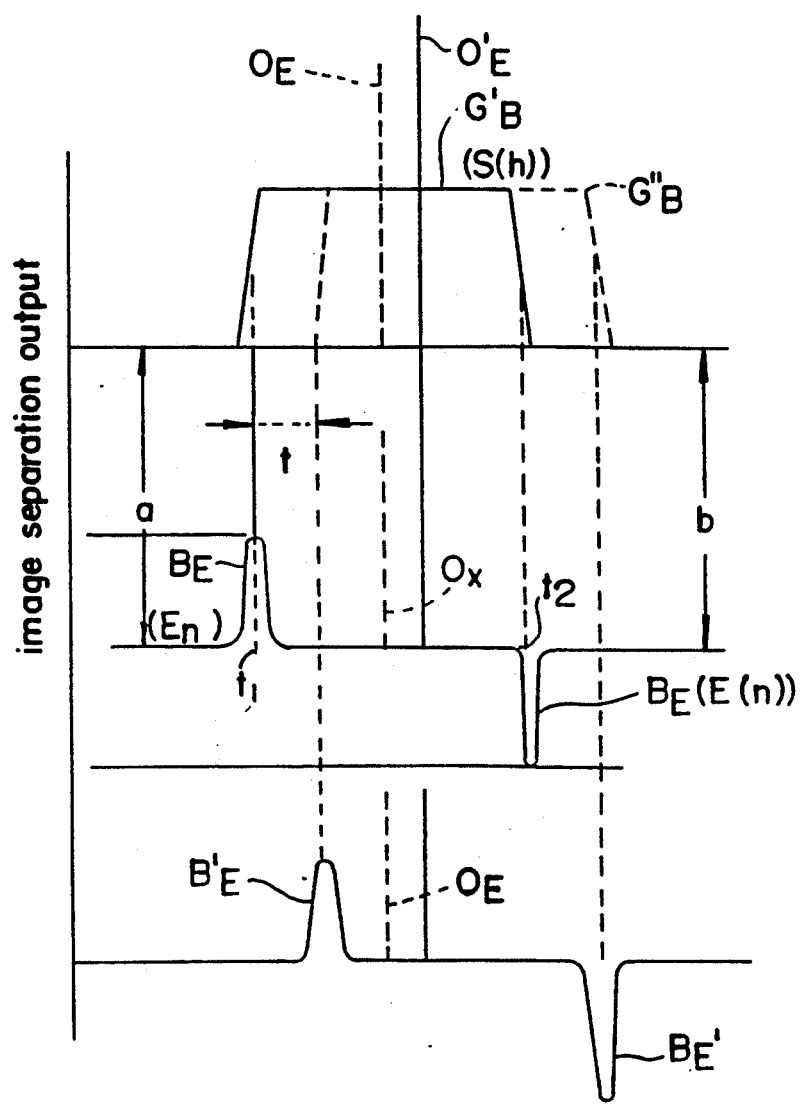

In this way, there can be obtained an integrate output as shown in FIG. 32.

Next, if the coordinate where E(n) becomes the largest is represented by $t_1$ and if the coordinate where E(n) becomes the smallest is represented by $t_2$, it can be anticipated that the gravity position is generally $(t_2+t_2)/2$.

Therefore, the inverse separation output at the time when the positional coordinate is inversed is represented by $G_3''$ to generate the difference output R(n). The integrate output $B_E'$ corresponding to the difference output R(n) becomes something like that shown by the solid line. If all bit numbers are represented by m here and if the correlation method calculation for finding the phase difference of R(n) with respect to S(n) is carried out with respect to before and after $m-(t_1+t_2)$, the gravity position can be found. In the same manner, the phase difference between $B_E$ and $B_E'$ can be found.

If the phase difference of R(n) with respect to S(n) or the phase difference between $B_E$ and $B_E'$ is represented by t, the gravity position from the central coordinate $O_E'$ of the sensor of S(n) can be found from t/2.

By using such calculation algorithm, there can be realized an eye direction detecting apparatus with high accuracy.

Unless the method for finding the phase difference between $B_E$ and $B_E'$ is employed, since R(n) is corresponds with the address of the memory in which S(n) is stored, if the data is called in the reverse order from the address, it is not necessary to form a memory zone for generating R(n) and, thus, the memory can be saved.

Furthermore, since the object is to find the largest and smallest addresses regarding the generation of E(n) and since the object is not to obtain E(n), the generating zone thereof is not necessary, either.

In the optical system of the eye direction detecting apparatus 246 of the above-mentioned example, since the light transferring system 246A and the light receiving system 246B are built in the camera body at the opposite side of the finder magnifier with the penta prism 240 as the boundary line, the reflecting light based on the refracting surfaces of various optical elements which constitute the light transferring system 246A and the light receiving system 246B is guided to the light receiving system 246B as a ghost, and a ghost as well as the first Purkinje image PI are formed on the primary line sensor 253 of the light receiving system 246B. Therefore, there still remains a problem in that it is difficult to distinguish the ghost and the first Purkinje image PI.

Therefore, an optical system of an eye direction detecting apparatus of a camera which is designed so that the ghost is not guided to the light receiving system 246B by every means will now be described.

FIGS. 33 through 37 illustrate an optical system of an eye direction detecting apparatus of a camera which is designed so that the ghost is not guided to the light receiving system 246B by every means. In the figures, identical component elements to those of the optical system shown in FIG. 13 are denoted by identical or similar reference numerals.

In this embodiment, the light transferring system 246A includes a light source 248 for emitting an infrared light, a total reflection mirror 149, and a collimator lens 150. The collimator lens 150 is aspherical at its surface. The infrared light emitted by the light source 248 is reflected by the total reflection mirror 149 and guided to the collimator lens 150. The collimator lens 150 is provided at its outgoing side surface with a diaphragm 151. The collimator lens 150 has such a function as to convert the infrared light emitted by the light source 248 into a parallel pencil of rays.

At the side where an eye 245 of the finder magnifier 244 is faced with, there is provided a coaxis forming, or light path overlapping optical member 152 for making the optical axis $l_i$ of the light transferring system 246A and the optical axis $l_j$ of the light receiving system 246B as a coaxis. In this embodiment, the coaxis forming optical system 152 comprises a rectangular parallelepiped comprising prisms 154 and 155 having a reflecting surface 153. The coaxis forming optical member 152 has a transmitting surface 156 facing the eye 245, a transmitting surface 157 opposite the transmitting surface 156 with the reflecting surface 153 sandwiched therebetween, and a transmitting surface 157' facing the collimator lens 150. The transmitting surface 156 is provided with a mask 158.

In this embodiment, in order to avoid the ghost based on the reflection at various transmitting surfaces of the coaxis forming optical member 152, the transmitting surfaces 156 and 157 are slightly inclined with respect to the optical axis $l_x$, whereas the transmitting surface 157' is slightly inclined with respect to the optical axis $l_i$. The inclination angles of the various transmitting surfaces 156, 157 and 157' with respect to the various optical axes $l_x$ and $l_i$ are 1° in this embodiment. Since the various transmitting surfaces 156, 157 and 157' have the same inclination angles, it becomes the same as the state where the parallel plane is inserted, and the aberration due to the inclination is hardly changed.

The reflecting surface 153 employed in this embodiment is of the type for semi-transmitting an infrared light and for transmitting a visible light. Since the reflecting surface 153 transmits a visible light, the photographer can see an image of the object formed on a focusing plate 242. The parallel pencil of rays passed through the diaphragm 151 is reflected by the reflecting surface 153 in the direction toward the eye 245 and projected to the eye 245 of the photographer placed on an eye point. In this embodiment, although it is used as the coaxis forming optical member 152, a mirror of the type for semi-transmitting an infrared light and for transmitting a visible light may be employed.

The corneal specular reflection beam of light for forming the first Purkinje image PI and the reflecting beam of light from the retina are guided again to the coaxis forming optical member 152, passed through the reflecting surface 153 and then guided to the finder magnifier 244. The finder magnifier 244 comprises lenses 244a and 244b in the same manner as mentioned.

In this embodiment, the light receiving system 246B comprises a compensator prism 159, a reducing lens 250, a total reflection mirror 161, a reimaging lens 252, and a primary line sensor 253. The reimaging lens 252, as shown in FIG. 35 in its enlarged scale, is provided on the surface at the side facing with the primary line sensor 253 with a mask 254 which is of the same constitution as already mentioned.

Figure 36:
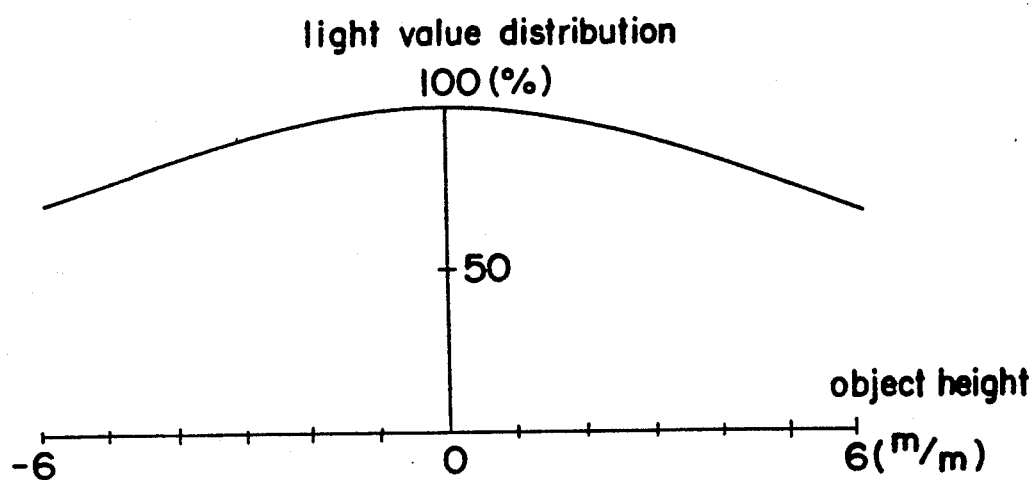
Figure 37:
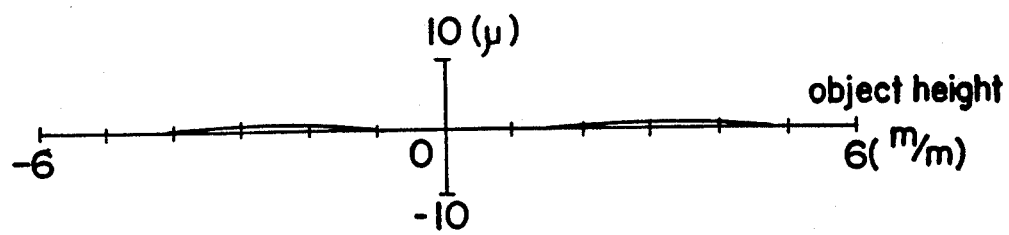

In this embodiment, the light receiving system 246B is preferably provided with no distortion and has preferably a generally uniform light amount distribution on the primary line sensor 253 in view of the object height. If the optical system is constituted in a way as will be described hereinafter, as shown in FIG. 36, the light amount distribution on the primary line sensor 253 can be generally equally covered within the range of the required object height. In addition, as shown in FIG. 37, the distortion can be made $1\mu$ or less.

By way of example only, presented below are various design values that may be used in light transferring system 246A:

Radius of curvature of the outgoing surface of the light source 248 . . . infinite;
Distance along the optical axes of the outgoing surface of the light source 248 and the total reflection mirror 149 . . . 7.7 mm;
Distance between the total reflection mirror 149 and the surface A of the collimator lens 150 . . . 7.3 mm
COLLIMATOR LENS 150
  Radius of curvature of the surface A . . . 10.00 mm
  Radius of curvature of the surface B . . . −28.00 mm
  Refractive index . . . 1.48304
  Center thickness . . . 4.00 mm
Distance along the optical axes between the mask 151 and the surface B of the collimator lens 150 . . . 0.00 mm
MASK 151
  Thickness . . . 0.04 mm
  Radius of curvature . . . infinite
Distance along the optical axes of the mask 151 and the transferring surface . . . 0.66 mm
TRANSMITTING SURFACE 157'
  Radius of curvature . . . infinite
  Inclination with respect to the optical axis $l_i$ . . . 1°
  Refractive index of the coaxis forming optical member 152 . . . 1.50871
Distance along the optical axes from the transmitting surface 157' to the transmitting surface 156 . . . 12 mm
TRANSMITTING SURFACE 156
  Radius of curvature . . . infinite
  Inclination with respect to the optical axis $l_x$ . . . 1°
Distance along the optical axes from the transmitting surface 156 to the cornea 232 . . . 13 mm
Radius of curvature of the cornea 232 . . . 7.980 mm
The surface A of the collimator lens 150 is aspherical and designed by finding the sag amount X from the following imaging formula of an aspheric lens;

$$X(a_4h + a_6h^6) + c \cdot h^2/(1 + \sqrt{1 - (k + 1)c^2 \cdot h^2})$$

wherein c is an inverse number of the radius of curvature of the surface A of the collimator lens 150, h is the object height from the optical axis $l_i$, and k is an aspheric coefficient, and $K = -3.165$, $a_4 = -2.95 \times 10^{-5}$ and $a_6 = 0$.

By way of example only, presented below are various design values that may be used in light receiving system 246B:

Radius of curvature of the cornea 232 . . . −7.980 mm
  Distance along the optical axes from the cornea 232 to the transmitting surface 156 . . . 13 mm
TRANSMITTING SURFACE 156
  Inclination with respect to the optical axis $l_x$ . . . −1°
  Radius of curvature . . . infinite
  Refractive index of the coaxis forming optical member 152 . . . 1.50871
Distance along the optical axes of the transmitting surfaces and 157 . . . 10 mm
TRANSMITTING SURFACE
  Inclination with respect to the optical axis $l_x$ . . . −1°
  Radius of curvature . . . infinite
Distance along the optical axes from the transmitting surface 157 to the surface A of the lens 244a . . . 0.60 mm
LENS 244a
  Radius of curvature of the surface A . . . 115.895 mm
  Center wall thickness . . . 1.2 mm
  Refractive index . . . 1.69747
  Radius of curvature of the surface B . . . 29.210 mm
LENS 244b
  Radius of curvature of the surface B . . . 29.210 mm
  Center wall thickness . . . 4.92 mm
  Refractive index . . . 1.61187
  Radius of curvature of the surface C . . . −47.880 mm
Distance along the optical axes from the surface C to the surface A of the pentagonal prism 240 . . . 1.00 mm
PENTAGONAL PRISM 240
  Radius of curvature of the surface A . . . infinite
  Refractive index . . . 1.50871
  Radius of curvature of the surface B . . . infinite
  Inclination of the surface B with respect to the optical axis $l_k$ . . . −24°
  Distance along the optical axes from the surface A to the surface B . . . 28.80 mm
Distance along the optical axes of the surface B and the surface A of the compensator prism 159 . . . 0.14 mm
COMPENSATOR PRISM 159
  Radius of curvature of the surface A . . . infinite
  Inclination of the surface A with respect to the optical axis $l_j$ . . . −24°
  Radius of curvature of the surface B . . . infinite
  Distance along the optical axes of the surfaces A and B . . . 3 mm
  Refractive index . . . 1.50871
Distance from the surface A to the mask 159' . . . 0 mm
MASK 159'
  Thickness . . . 0.04 mm
  Radius of curvature . . . infinite
Distance of the optical axes from the mask 159' to the surface A of the reducing lens 250 . . . 0.10 mm
REDUCING LENS 250
  Radius of curvature of the surface A . . . 11.716 mm
  Wall thickness . . . 2.50 mm
  Radius of curvature of the surface B . . . −60.140 mm
  Refractive index . . . 1.48304
Distance along the optical axes from the surface B to the total reflection mirror 161 . . . 3.00 mm
Radius of curvature of the total reflection mirror 161 . . . infinite
Distance along the optical axes from the total reflection mirror 161 to the reimaging lens 252 . . . 7.60 mm
REIMAGING LENS 252
  Radius of curvature of the surface A . . . 1.520 mm
  Refractive index . . . 1.48304 mm
  Center wall thickness . . . 1.520 mm
  Radius of curvature of the surface B . . . infinite
  Distance from the surface B to the mask 254 . . . 0.00 mm
MASK 254

Radius of curvature ... infinite
Wall thickness ... 0.04 mm

The surface A of the reducing lens 250 is aspheric and designed according to the afore-mentioned formula but under the condition of $K=-1.25$, $\alpha_4=-8\times10^{-5}$ and $\alpha_6=-10^{-6}$.

Figure 38:
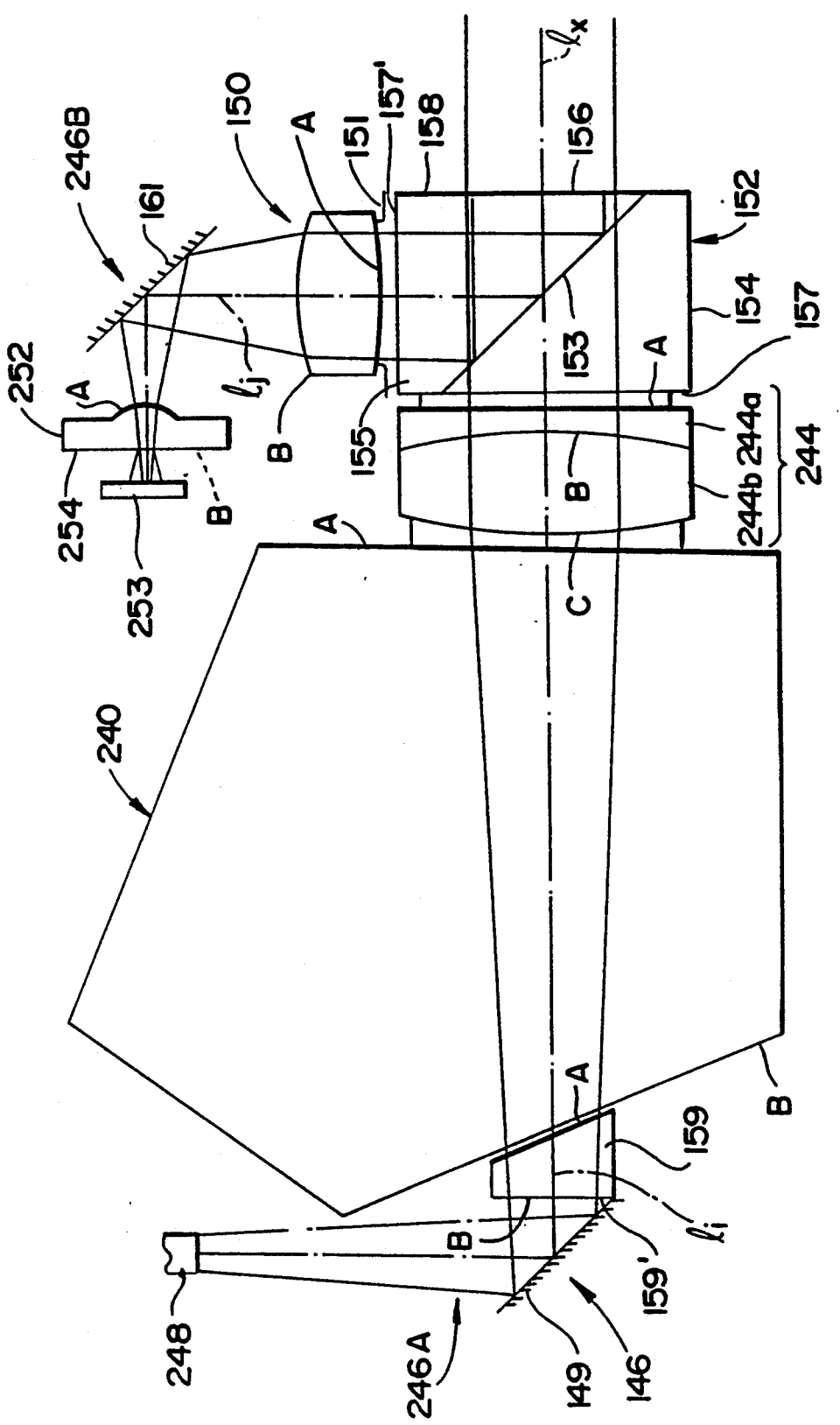
Figure 39:
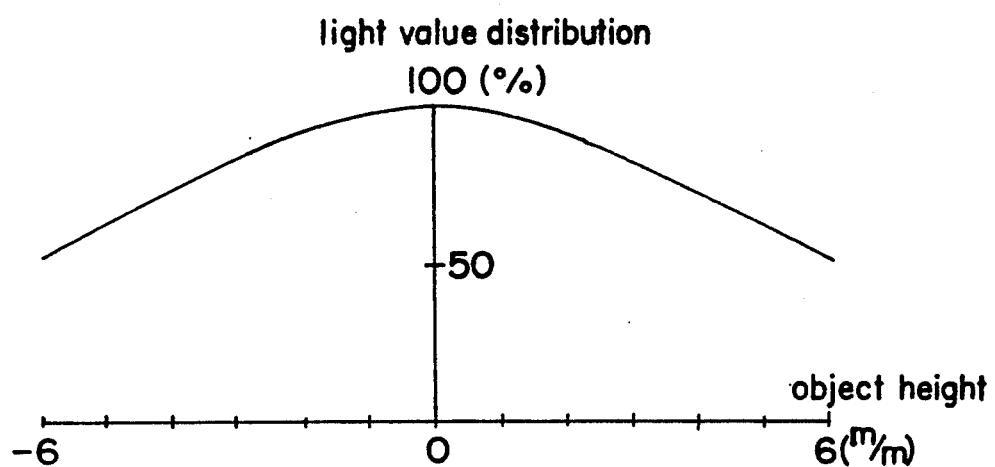
Figure 40:
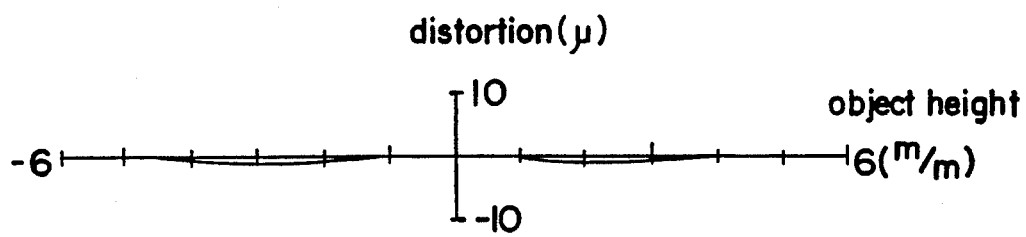

FIGS. 38 through 40 illustrate a second embodiment of an eye direction detecting optical apparatus of a camera according to the present invention. In this embodiment, a light transferring system 246A is disposed opposite a finder magnifier 244 with a pentagonal prism 240 placed therebetween, and a light receiving system 246B is disposed at the side of a transmitting surface 157' of a coaxis forming optical member 152, so that the infrared light emitted by a light source 248 is guided to the finder magnifier 244 through a compensator prism 159 and the pentagonal prism 240. The infrared light is converted into a parallel pencil of rays by the finder magnifier 244 and projected to the eye 245. The beam of light for forming the first Purkinje image PI based on the corneal specular reflection of the eye 245 and the reflecting light from the retina are reflected by a reflecting surface 153 of the coaxis forming optical member 152 and then guided to the light receiving system 246B. All the remaining optical component elements are generally the same as the first embodiment and the optical characteristics thereof are also generally the same as the first embodiment as shown in FIGS. 11 and 12. Therefore, design values thereof are merely stated hereunder.

(1) DESIGN VALUES OF THE LIGHT TRANSFERRING SYSTEM 246A: (EXAMPLES ONLY)

Radius of curvature of the outgoing surface of the light source 248 ... infinite
  Distance along the optical axes of the outgoing surface of the light source 248 and the total reflection mirror 149 ... 17 mm
  Radius of curvature of the total reflection mirror 149 ... infinite
  Distance along the optical axes of the total reflection mirror 149 and the mask 159' ... 3 mm
MASK 159'
  Wall thickness ... 0.04 mm
  Radius of curvature ... infinite
Distance between the mask 159' and the surface B of the compensator prism 159 ... 0.00 mm
COMPENSATOR PRISM
  Radius of curvature of the surface B ... infinite
  Distance between the surfaces A and B ... 3 mm
  Radius of curvature of the surface A ... infinite
  Inclination of the surface A with respect to the optical axis $l_i$ ... 24°
Distance along the optical axes of the surface A and the surface B of the pentagonal prism 240 ... 0.14 mm
PENTAGONAL PRISM 240
  Radius of curvature of the surface B ... infinite
  Inclination of the surface B with respect to the optical axis $l_i$ ... 24°
  Refractive index ... 1.50871
  Radius of curvature of the surface A ... infinite
Distance between the axes from the surface A to the surface B ... 28.80 mm
Distance between the axes of the surface A and the surface C of the lens 244b ... 1.00 mm
LENS 244b
  Radius of the curvature of the surface C ... 47.880 mm
  Radius of the curvature of the surface B ... −29.210 mm
  Center wall thickness ... 4.92 mm
  Refractive index ... 1.61187
LENS 244a
  Radius of the curvature of the surface B ... −29.210 mm
  Radius of the curvature of the surface A ... −115.895 mm
  Center wall thickness ... 1.2 mm
  Refractive index ... 1.69747
Distance along the optical axes of the surface A and the transmitting surface 157 ... 0.60 mm
TRANSMITTING SURFACE 157
  Radius of the curvature ... infinite
  Inclination with respect to the optical axis $l_i$ ... 2°
  Refractive index of the coaxis forming optical member 152 ... 1.50871
Distance along the optical axes from the transmitting surface 157 to the transmitting surface 156 ... 10 mm
TRANSMITTING SURFACE 156
  Radius of the curvature ... infinite
  Inclination with respect to the optical axis $l_x$ ... 2°
Distance along the optical axes from the transmitting surface 156 to the cornea 232 ... 13 mm
  Radius of the curvature of the cornea 232 ... 7.980 mm (2) DESIGN VALUES OF THE LIGHT RECEIVING SYSTEM 246B (EXAMPLES ONLY):
  Radius of the curvature of the cornea 232 ... −7.980 mm
Distance along the optical axes from the cornea 232 to the transmitting surface 156 ... 13 mm
TRANSMITTING SURFACE 156
  Radius of the curvature ... infinite
  Inclination with respect to the optical axis $l_x$ ... −2°

Distance along the optical axes from the transmitting surface 156 to the transmitting surface 157' ... 12 mm
Refractive index of the coaxis forming optical member 152 ... 1.50871
TRANSMITTING SURFACE 157'
  Inclination with respect to the optical axis $l_j$ ... −2°
  Radius of the curvature ... infinite
Distance along the optical axes from the transmitting surface 157' to the mask 151 ... 0.66 mm
Distance between the mask 151 and the reducing lens 250 ... 0.00 mm
MASK 151
  Radius of the curvature ... infinite
  Wall thickness ... 0.04 mm
REDUCING LENS 250
  Radius of the curvature of the surface A ... 28.00 mm
  Wall thickness ... 4.00 mm
  Radius of the curvature of the surface B ... −10.00 mm
  refractive index ... 1.48304
Distance along the optical axes from the surface B to the total reflection mirror 161 ... 7.30 mm
Radius of the curvature of the total reflection mirror 161 ... infinite
Distance along the optical axes of the total reflection mirror 161 and the surface A of the reimaging lens 252 ... 5.70 mm
REIMAGING LENS 252
  Radius of the curvature of the surface A ... 2.00 mm
  Refractive index ... 1.48304

Center wall thickness . . . 2.00 mm
Radius of the curvature of the surface B . . . infinite
Distance between the surface B to the mask 254 . . . 0.00 mm MASK 254
Radius of the curvature . . . infinite
Thickness . . . 0.04 mm The surface B of the reducing lens 250 is aspheric and is designed from the afore-mentioned formula but under the condition that $K = -3.165$, $\alpha_4 = 2.95 \times 10^{-5}$ and $\alpha_6 = 0$.

As those skilled in the art should appreciate, an optical system of an eye direction detecting apparatus of a camera constructed according to the teachings of the present invention will not allow a ghost to be guided to the internal light receiving system.

Many modifications and variations of this invention are possible in light of the above teachings. It therefore to be understood that within the scope of the appended claims, the invention may be practiced otherwise than as specifically described.

We claim:

1. An eye direction detecting apparatus for a camera, comprising:
    means for guiding substantially parallel rays of light through an eye piece element of a finer system of said camera towards said photographer's eye;
    a light receiving system having means for receiving a first Purkinje image, based on a specular reflection of the cornea of said eye and reflecting light from a retina of said eye, is formed, said receiving means generating a light receiving output; and
    a processing circuit for detecting the eye direction of said eye based upon said light receiving output of said receiving means.

2. The apparatus as recited in claim 1, wherein said eye includes a pupil and said pupil has a periphery, wherein said receiving means comprises a one-dimensional line sensor, wherein said processing circuit establishes a first coordinate corresponding to said periphery of said pupil by processing an output from one said one-dimensional line sensor in a first slice level, wherein said processing circuit establishes a second coordinate corresponding to said first Purkinje image by processing said output from said one-dimensional line sensor in a second slice level, and wherein said eye direction is detected by a calculation of coordinates with respect to said first and second coordinates.

3. The apparatus as recited in claim 1, wherein said receiving means comprises a one-dimensional line sensor, and wherein said processing circuit includes means for separating said output from said one-dimensional line sensor into a retina reflecting light corresponding output composition corresponding to a reflecting light from the retina and a first Purkinje image forming reflecting light corresponding output composition corresponding to a reflecting light for forming the first Purkinje image and for finding a center coordinate of the separated retina reflecting light corresponding to the composition and a center coordinate of the first Purkinje image forming reflecting light, thereby to detect the eye direction, respectively.

4. The apparatus as recited in claim 3, wherein said receiving means comprises a reimaging lens for reimaging reflecting light for forming said first Purkinje image on said one-dimensional line sensor based on a corneal specular reflection, and wherein said processing circuit includes a correcting means for correcting a decrease of a peripheral portion incident light amount based on the light amount distribution characteristics of said reimaging lens.

5. The apparatus as recited in claim 4, wherein the position of the first Purkinje image and the position of the pupil are established by bit inverting said separated retina reflecting light corresponding output composition and said first purkinje image forming reflecting light corresponding output composition.

6. An eye direction detecting apparatus of a camera, comprising:
    a light transferring system for radiating a detecting light in the form of a beam of substantially parallel rays of light that pass through a light path overlapping optical member of a finder of said camera towards an eye of a photographer looking into said light path overlapping optical member; and
    a light receiving system having means for reimaging said detecting light, for forming a virtual image based upon a corneal specular reflection of the eye, wherein said light path overlapping optical member makes an optical path of said light transferring system overlap with an optical path of said light receiving system.

7. The apparatus as recited in claim 6, wherein said light receiving system comprises a reducing lens and a reimaging lens disposed between said coaxis forming optical member and said light receiving portion, and wherein said reducing lens has at least one aspherical surface.

8. The apparatus as recited in claim 6, wherein said light path overlapping optical member comprises a mirror which permits visible light to pass therethrough and which has a reflecting and transmitting characteristic with respect to infrared light.

9. The apparatus as recited in claim 6, wherein said light path overlapping optical member comprises a prism.

10. The apparatus as recited in claim 9, wherein said prism has a first transmitting surface facing said eye, a second transmitting surface opposite said first transmitting surface, and a reflecting surface disposed between said first transmitting surface and said second transmitting surface and facing said finder magnifier and, further, wherein first transmitting surface slightly inclined with respect to an optical axis of said light transferring system.

11. The apparatus of claim 6, wherein said light path overlapping optical member is located at a side of an eye piece lens of said finder that faces said photographer's eye.

12. The apparatus of claim 11, wherein said processing means determine said eye direction based on at least a first Purkinje image.

13. The apparatus of claim 11, wherein said processing means determines said eye direction based on a first Purkinje image and a pupil image.

14. An eye direction detecting optical system, comprising:
    a) a finder system of a camera having a viewing area with a plurality of zones to which an eye can be selectively directed, thereby defining an actual eye direction; and
    b) means for determining to which of said plurality of zones said eye is directed, thereby defining a determined eye direction, said means for determining comprising:

i) means for compensating for a difference between said determined eye direction and said actual eye direction.

15. The system as recited in claim 14, wherein said means for compensating for a difference between said determined eye direction and said actual eye direction comprises a means for compensating for a difference caused by light amount damping.

16. The system as recited in claim 15, wherein said means for compensating for a difference caused by light amount dampening comprises:
   a) means for determining an amount of light amount damping.

17. The system as recited in claim 16, wherein said means for compensating further comprises:
   b) means for generating a light amount correcting value based upon the determined amount of light amount damping by said means for determining.

18. The system as recited in claim 14, wherein said eye has a cornea and a retina, and wherein said means for determining further comprises:
   ii) means for directing light towards said eye, and
   iii) means for generating a light amount distribution including a first Purkinje image composition based on corneal specular reflection and a retinal reflecting composition based on reflecting light from said retina.

19. An eye direction detecting optical system, comprising:
   a) means for directing light rays towards an eye;
   b) means for receiving light rays reflected by said eye, said receiving means generating a light amount distribution;
   c) means for compensating for a damping of the amount of light received by said receiving means;
   d) means for determining a central position of said light amount distribution, after said compensating means compensates said light amount damping; and
   e) means for determining an eye direction based upon said determined central position.

20. An eye direction detecting apparatus, comprising:
   a finder system;
   means for directing light rays through said finder system towards an eye;
   means for receiving light rays through said finder system that are reflected by said eye, said means for receiving generating a light amount distribution having a center position;
   means for detecting said center position of said light amount distribution and producing an output; and
   processing means for determining eye direction based on said output of said center position detecting means.

21. The apparatus as recited in claim 20, wherein said eye has a cornea and a retina, wherein said light amount distribution has a corneal specular reflection component and a retina reflection light component.

22. The apparatus as recited in claim 21, wherein said processing means comprises means for determining a first phase difference between said corneal specular reflection component and said retina reflecting light component.

23. The apparatus as recited in claim 22, wherein said processing means further comprises means for inverting said corneal specular reflection component and said retina reflecting light component.

24. The apparatus as recited in claim 23, wherein said processing means further comprises means for determining a second phase difference between said inverted corneal specular reflection component and said inverted retina reflecting light component.

25. The apparatus as recited in claim 24, wherein said processing means further comprises means for calculating said gravity position based on said first phase difference and said second phase difference.

26. An eye direction detecting apparatus in combination with a camera, said apparatus being incorporated into said camera, said apparatus comprising:
   a finder system;
   means for directing light rays through said finder system towards an eye;
   means for receiving light rays through said finder system that are reflected by said eye, said means for receiving generating a light amount distribution having a center position;
   means for detecting said center position of said light amount distribution and producing an output; and
   processing means for determining eye direction based on said output of said center position detecting means.

27. An eye direction detecting apparatus, comprising:
   a light transferring system having a first optical path, said light transferring system projecting substantially parallel light rays towards and eye;
   a light receiving system having a second optical path, said light receiving system receiving light rays that are reflected from said eye;
   means for making said optical path of said light transferring system and said optical path of said light receiving system overlap; and
   means for preventing refracted light from forming a ghost image within said light receiving system.

28. The apparatus as recited in claim 27, wherein said means for making comprises an optical member having at least two transmitting surfaces, each of said at least two transmitting surfaces having an identical angle of inclination with respect to said coaxial axes.

29. The apparatus as recited in claim 28, wherein said light transferring system comprises means for emitting light, wherein said light receiving system comprises a light sensor, wherein said apparatus further comprises means for directing said emitted light into said eye, and wherein light reflected from said eye forms a light amount distribution of said light sensor.

30. The apparatus as recited in claim 29, wherein said eye has a cornea and a retina and wherein said light amount distribution has a corneal specular reflection component and a retina reflecting light component.

31. An eye direction detecting apparatus in combination with a camera, said apparatus being incorporated into said camera, said apparatus comprising:
   a light transferring system having a first optical path, said light transferring system projecting substantially parallel light rays towards and eye and comprising means for emitting light;
   a light receiving system having a second optical path, said light receiving system receiving light rays that are reflected from said eye and comprising a light sensor;
   means for making said optical path of said light transferring system and said optical path of said light receiving system overlap comprising an optical member having at least two transmitting surfaces, each of said at least two transmitting surfaces having an identical angle of inclination with respect to said coaxial axes;

means for preventing refracted light from forming a ghost image within said light receiving system; and means for directing said emitted light into said eye, wherein light reflected from said eye forms a light amount distribution on said light sensor, wherein said eye has a cornea and a retina and wherein said light amount distribution has a corneal specular reflection component and a retina reflecting light component.

32. An eye direction detecting device for a photographing camera, comprising:

means fur guiding a beam of light to a photographer's eye;

means for receiving a reflecting beam of light that is reflected from said photographer's eye, said receiving means providing an output;

means for detecting a position of a first Purkinje image formed by a specular reflection of a cornea of said eye based on said output;

means for detecting a center position of a pupil of said eye based upon said output; and means for determining an eye direction of said eye by calculating relative relation between said position of the first Purkinje image and the center position of the pupil.

33. The device of claim 32, wherein said means for receiving a reflecting beam of light comprises a one-dimensional line sensor.

34. The device of claim 32, wherein said means for receiving a reflecting beam of light and a cornea of said eye are in a substantially optically conjugate relation with each other.

35. The device of claim 33, further comprising means for separating an output signal from said one-dimensional line sensor into a retina reflecting light corresponding output composition that corresponds to light reflected from the retina of said eye and a first Purkinje image forming reflecting light corresponding output composition that corresponds to said reflected beam of light for forming the first Purkinje image and means for finding a center position of the separated retina reflecting light and the center position of said first Purkinje image forming reflecting light, respectively.

36. The device of claim 33, wherein a reimaging lens reimages said reflected light beam.

37. The device of claim 36, wherein said reimaging lens comprises a cylindrical lens, said reimaging lens elongating an image formed with said light reflected from said eye, an elongating direction being in a direction perpendicular to an arrangement of elements of said one-dimensional line sensor.

38. The device of claim 33, wherein said one-dimensional line sensor has a narrow width in an arrangement direction of elements of said sensor and a broad width perpendicular to said arrangement direction.

39. The device of claim 32 wherein said means receiving a reflecting beam of light employs a cylindrical reimaging lens, said reimaging lens elongating said light that is reflected from said photographer's eye so that an image is formed by said reflected light on a one-dimensional line sensor, irrespective of an alignment of said eye with said eye piece element of a finder system.

40. The device of claim 32, wherein said guiding means comprises:

a light source for emitting said beam of light towards said eye;

a half mirror through which said beam of light passes; and a minifying lens that functions to reduce the optical path length of said eye direction detecting device.

41. The device of claim 40 wherein said light source comprises an infrared light source.

42. The device of claim 40, wherein said reflected beam of light is reflected off said half mirror and focused onto a light sensor by a reimaging lens.

43. The device of claim 42, wherein said light sensor comprises a one-dimensional photosensitive element.

44. The device of claim 32, wherein said guiding means comprises:

a light source for emitting said substantially parallel beam of light; and a half mirror for reflecting said beam of light towards said eye.

45. The device of claim 44, wherein said light source comprises an infrared light source.

46. The camera of claim 44, wherein said reflected beam of light is passed through said half mirror and focused onto a light sensor by a reimaging lens.

47. The device of claim 46, wherein said light sensor comprises a one-dimensional photosensitive element.

48. The device of claim 46, wherein a cornea of said photographer and said light source are in a substantially optically conjugate relation with each other.

49. The eye direction detecting device of claim 32, wherein said means for determining an eye direction determines the direction said eye gazes at based upon at least two coordinates, said coordinates changing according to a revolving of said eye.

50. The eye direction detecting device of claim 49, wherein one of said coordinates corresponds to a first Purkinje image, based upon a specular reflection of a cornea of said eye.

51. The eye direction detecting device of claim 50, wherein one of said coordinates corresponds to said first Purkinje image and the remaining coordinates correspond to a pupil image, based upon a reflecting light from a retina of said eye.

52. An eye direction detecting device for determining a direction in which a photographer's eye looks, comprising:

a light source;

a finger system having an eyepiece element;

means for guiding a beam of light from said light source through said eyepiece element of a finder system so that said light beam impinges upon an eye of photographer that is placed proximate said eyepiece;

a sensor for detecting a beam of light reflected from said photographer's eye and which passes through said eyepiece element, said sensor producing an output signal, wherein said sensor comprises a one-dimensional line sensor; and means for processing said output signal to determine the direction in which said eye looks.

53. The device of claim 52, further comprising a cylindrical reimaging lens, said remaining lens elongating an image formed with said light reflected said eye, in an elongating direction that is perpendicular to an arrangement of elements of said one-dimensional line sensor.

54. An eye direction detecting device for determining a direction in which a photographer's eye looks, comprising:

a light source;

a finder system having an eyepiece element;

means for guiding a beam of light from said light source through said eyepiece element of a finder system so that said light beam impinges upon an eye of a photographer that is placed proximate said eyepiece;

a sensor for detecting a beam of light reflected from said photographer's eye and which passes through said eyepiece element, said sensor producing an output signal, wherein a cornea of said eye and said sensor are in a substantially optically conjugate relation with each other, wherein said sensor comprises a one-dimensional line sensor;

means for processing said output signal to determine the direction in which said eye looks; and a cylindrical reimaging lens, said reimaging lens elongating an image formed with said light reflected from said eye in an elongating direction that is perpendicular to an arrangement of elements of said one-dimensional line sensor.

55. An eye direction detecting device for determining a direction in which a photographer's eye looks, comprising:

a light source;

a finder system having an eyepiece element;

means for guiding a beam of light from said light source through said eyepiece element of a finder system so that said light beam impinges upon an eye of a photographer that is placed proximate said eyepiece;

a sensor for detecting a beam of light reflected from said photographer's eye and which passes through said eyepiece element, said sensor producing an output signal, wherein a cornea of said eye and said sensor are in a substantially optically conjugate relation with each other;

means for processing said output signal to determine the direction in which said eye looks, wherein said processing means includes means for correcting a decrease of a peripheral portion incident light amount based on a light amount distribution characteristics of said reimaging lens.

56. An optical focus detecting device for a camera, comprising:

a center focus condition detecting system for detecting a focus condition of a lens in a center zone of an image equivalent plane;

a plurality of peripheral focus detection systems for detecting focus conditions of said lens in peripheral zones of said image equivalent plane, said peripheral zones being different from said center zones, each focus condition detecting system having an image splitting element for splitting and reimaging said image formed with said lens, and a pair of photoelectric detecting means that receives each split image;

means for detecting a direction at which a photographer's eye looks;

means for selecting one of said peripheral zones or center zone according to said direction detected by said eye direction detecting means;

processing means for detecting said focus condition of said lens in said selected zone, said processing means comparing output signals from said selected pair of photoelectric detecting means; and a lens driving mechanism for moving said lens to bring said lens in focus, based upon an output signal from said processing means.

57. The device of claim 56, wherein said detecting optical system has an infrared light source for emitting an infrared light, said infrared light being guided to said eye through a finder magnifying lens.

58. An eye direction detecting device, comprising:

means for emittting light toward an eye; and a one-dimensional line sensor for detecting relative positions between a corneal image and a pupil image, each formed by a reflection from respective portions of said eye, said relative positions being indicative of a viewing direction of said eye.

59. An eye direction detecting device, comprising:

a viewing area, said viewing area having a viewing area axis, while an eye of a user has an optical axis;

means for directing light rays along said optical axis toward said viewing area and adapted to be directed toward said eye; and a predetermined one-dimensional means for receiving light rays reflected by said eye for determining an angular relationship between said viewing area axis and said optical axis of said eye.

60. The eye direction detecting device of claim 59, wherein said means for receiving light rays reflected by said eye comprises means for detecting a corneal image and a pupil image.

61. The eye direction detecting device of claim 60, wherein said means for receiving light rays further comprises a one-dimensional line sensor which detects and produces an output signal that is indicative of respective positions of said corneal image and said pupil image.

62. The eye direction detecting device of claim 1 wherein said one-dimensional line sensor is adapted to be in an optically conjugate position with said pupil of said eye when said eye is positioned adjacent said viewing area.

63. The eye direction detecting device of claim 61, wherein said means for determining said angular relationship between said viewing area axis and said optical axis of said eye comprises means for processing said output signal from said one-dimensional line sensor, said system further comprising means for storing said processed output signal.

64. The eye direction detecting device of claim 63, wherein said viewing area comprises a view finder having a plurality of zones through which said eye can look, whereby said eye direction detecting device comprises means for detecting through which of said plurality of zones said eye is looking, said eye direction detecting device further comprising a lens and means for focusing said lens.

65. The eye direction detecting device of claim 64, further comprising a plurality of auto focus optical systems for respective ones of said plurality of view finder zones for automatically focusing said lens, wherein said means for focusing said lens comprises means for driving one of said plurality of auto focus optical systems based upon which of said plurality of view finder zones that said eye is looking, as determined by said detecting means.

66. The eye direction detecting device of claim 65, further comprising means for driving a respective one of said auto focus optical systems as a function of said angular relationship between said viewing area axis and said optical axis of said eye.

67. An eye direction device of a camera, comprising:

a viewing area having at least a predetermined zone to which an eye can be directed, said viewing area being disposed in a finder system of said camera;

means for guiding rays of light towards a photographer's eye;

means for detecting reflecting rays of light that are reflected from said photographer's eye and for providing an output;

means for determining said eye is directed to said predetermined zone based on the output of said detecting means; and means for operating a predetermined function of said camera in response to said determining means determining that said eye is directed to said predetermined zone.

68. The eye direction detecting device of claim 67, further comprising means for generating a plurality of signals, each of which is dependent upon and is unique to the detection of a respective zone to which said eye is directed.

69. The eye direction detecting device of claim 68, further comprising means for moving that is responsive to said detection of said zone at which said eye is detected to be directed.

70. The eye direction detecting device of claim 68, wherein said means for determining to which of said plurality of zones said eye is directed comprises a light source for directing light toward said eye, and a one-dimensional line sensor on which an image of said eye is formed.

71. The eye direction detecting device of claim 70, wherein said one-dimensional line sensor is substantially conjugate with said eye when said eye is positioned adjacent said viewing area.

72. The eye direction detecting device of claim 70, further comprising means for forming a corneal image and a pupil image on said one-dimensional line sensor, and wherein said means for determining to which of said plurality of zones said eye is directed comprises means for determining the relative positions between said corneal image and said pupil image.

73. The eye direction detecting device of claim 70, wherein said light source directs light through said viewing area.

74. The eye direction detecting device of claim 73, wherein said light source emits infrared light.

75. The eye direction detecting device of claim 73, further comprising an imaging optical system for forming said image of said eye of said image receiving element.

76. The eye direction detecting device of claim 75, wherein said imaging optical systems further comprises a minifying lens and a reimaging lens which directs said image of said eye on said one-dimensional line sensor.

77. The eye direction detecting device of claim 76, further comprising a mask attached to said reimaging lens, said mask having an opening, said reimaging lens having a center of curvature, and wherein said opening has a center at said center of curvature of said reimaging lens.

78. The eye direction detecting device of claim 76, wherein said reimaging lens has a center or curvature, and wherein said minifying lens has a focal point located in said center of curvature of said reimaging lens.

79. The eye direction detecting device of claim 78, wherein said minifying lens comprises an aspherical surface.

80. The eye direction detecting device of claim 70, wherein said zones of said viewing area are arranged substantially along a predetermined line, and wherein said one-dimensional line sensor extends substantially parallel to said predetermined line.

81. The eye direction detecting device of claim 80, further comprising an imaging optical system for forming said image of said eye which includes means to direct said image of said eye on said one-dimensional line sensor.

82. The eye direction detecting device of claim 81, wherein said means to direct said image comprises means for elongating said image in a direction that is substantially perpendicular to said one-dimensional line sensor.

83. The eye direction detecting device of claim 67, wherein said predetermined function of said camera comprises focusing said camera.

84. The eye direction detecting device of claim 67, wherein said viewing area of said finder system of said camera comprises a plurality of predetermined zones to which an eye can be directed, and wherein said means for determining comprises means for determined which of said plurality of predetermined zones said eye is directed.

85. An eye direction detecting device, comprising:
a viewing area;
a plurality of zones located in said viewing area;
a plurality of auto focus optical systems, each of which corresponds to a respective one of said plurality of viewing area zones;
a main lens having an exit pupil with at least two aperture zones defined by said plurality of auto focus optical systems;
means for automatically selecting one of said plurality of auto focus optical systems; and
means for driving said automatically selected one of said plurality of auto focus optical systems for focusing said main lens, wherein said means for automatically selecting one of said plurality of auto focus optical systems comprises means for detecting the direction of one's eye relative to a predetermined position.

86. An eye direction detecting device, comprising:
a viewing area;
a plurality of zones located in said viewing area;
a plurality of auto focus optical systems, each of which corresponds to a respective one of said plurality of viewing area zones;
a main lens having an exit pupil with at least two aperture zones defined by said plurality of auto focus optical systems;
means for automatically selecting one of said plurality of auto focus optical systems; and
means for driving said automatically selected one of said plurality of auto focus optical systems for focusing said main lens, wherein said means for automatically selecting one of said plurality of auto focus optical systems comprises means for determining to which of said plurality of zones an eye is directed.

87. An eye direction detecting device, comprising:
means for guiding a beam of light that is reflected from said photographer's eye, wherein said reflecting beam detecting means includes a one-dimensional line sensor for detecting said reflecting beam of light, said one-dimensional line sensor providing an output signal; and means for determining the direction in which said eye gazes, based on the output signal of said one-dimensional line sensor;

wherein said one-dimensional line sensor extends in a predetermined direction, and wherein said reflecting beam detecting means includes an anamorphic reimaging lens, said anamorphic reimaging lens forming an image elongated in a direction generally perpendicular to the predetermined direction in which said one-dimensional line sensor extends.

88. An eye direction detecting device according to claim 87, wherein said anamorphic lens comprises a cylindrical lens.

89. An eye direction detecting device built in a finder of a camera having a pentagonal prism and eyepiece, said eye direction detecting device comprising:
   means for guiding a beam of light towards a photographer's eye;
   means for detecting a reflecting beam of light that is reflected from said photographer's eye, said reflecting beam being mounted on another side of the pentagonal prism, said separated beam detecting means providing an output; and
   means for determining the direction in which said eye gazes based on the output of said separated beam detecting means.

90. An eye direction detecting device built ihn a finder of a camera having a pentagonal prism and eyepiece, said eye direction detecting device comprising:
   a light source that is located outside of an optical path of said finder;
   means for guiding a beam of light from said light source towards a photographer's eye, said means for guiding being mounted on one side of the pentagonal prism;
   means for separating a reflected beam of light that is reflected from said photographer's eye to outside of said optical path of said finder;
   means for detecting a separated beam of light that is separated by said reflected beam separating means, said beam detecting means being mounted on another side of the pentagonal prism, said separated beam detecting means providing an output; and
   means for determining the direction in which said eye gazes based on the output of said separated beam detecting means.

91. A camera having an eye direction detecting apparatus for effecting focusing of a selected one of a plurality of auto focus optical systems, said camera comprising:
   a finder having a plurality of finder zones;
   a plurality of auto focus optical systems respectively corresponding to said plurality of finder zones, each of said plurality of auto optical focus systems corresponding to a respective one of said plurality of finder zones;
   a photographic lens having an exit pupil optically aligned with said plurality of auto focus optical systems;
   said plurality of auto focus optical systems having at least one photoelectronic device for producing an output signal, said output signal produced by said photoelectric device for moving said photographic lens automatically to bring said camera into focus;
   an eye direction detecting apparatus for detecting a direction of a photographer's eye looking into the finder for detecting which of said plurality of finder zones the photographer's eye is looking; and
   means for selecting a respective one of said plurality of auto focus optical systems in response to detection of the finder zone that the photographer's eye is looking.

92. An eye direction detecting device of a camera, comprising:
   a finder system that is built in said camera;
   a light source for illuminating an eye of a photographer, said light source being mounted in a finder;
   an imaging optical system for imaging a beam of light reflected from said photographer's eye, said imaging optical system having a mask for limiting a scope of a beam of light passing through said imaging optical system;
   a sensor for detecting an image formed by said imaging optical system, said sensor producing an output signal; and
   means for processing said output signal to determine the direction in which said eye looks.

93. An eye detecting device built in a finder of a camera having a pentagonal prism and eyepiece, said eye direction detecting device comprising:
   means for guiding a beam of light towards a photographer's eye;
   means for detecting a reflecting beam of light that is reflected from said photographer's eye, said reflecting beam of light detecting means providing an output; and
   means for determining the direction in which said eye gazes based on the output of said reflecting beam detecting means;
   wherein both of said beam guiding means and said beam detecting means are mounted on an upper side of said camera and on one side of said pentagonal prism.

94. The eye direction detecting device of claim 92, wherein said one side of said pentagonal prism is a side opposite of said pentagonal prism opposite from said eyepiece.

* * * * *

UNITED STATES PATENT AND TRADEMARK OFFICE
CERTIFICATE OF CORRECTION

PATENT NO. : 5,327,191            Page 1 of 3
DATED : July 5, 1994
INVENTOR(S) : Osamu SHINDO et al.

It is certified that error appears in the above-indentified patent and that said Letters Patent is hereby corrected as shown below:

At the cover sheet, section [30], line 4 under Foreign Application Priority Data, change "Dec. 17, 1988" to -- Dec. 17, 1987 --.
    At column 29, line 26 (claim 1, line 4), change "finer" to --finder --.
    At column 34, line 26 (claim 48, line 4), change "source" to -- sensor --.
    At column 34, line 46 (claim 52, line 5), change "finger" to -- finder --.
    At column 36, line 23 (claim 60, line 1), change "59" to -- 58 --.
    At column 36, line 33 (claim 62, line 1), change "1" to -- 61 --.
    At column 37, line 48 (claim 75, line 3), change "of" (second occurrence) to -- on ---.
    At column 37, line 53 (claim 76, line 2), change "systems" to -- system --.
    At column 37, line 63 (claim 78, line 2), change "or" to -- of --.
    At column 39 of the patent, delete lines 14 through 26 in their entireties (claim 89 in its entirety) and insert the following corrected claim:

--89. An eye direction detecting device built in a finder of a camera having a pentagonal prism and eyepiece, said eye direction detecting device comprising:
    means for guiding a beam of light towards a photographer's eye;

UNITED STATES PATENT AND TRADEMARK OFFICE
CERTIFICATE OF CORRECTION

PATENT NO. : 5,327,191
DATED : July 5, 1994
INVENTOR(S) : Osamu SHINDO et al.

Page 2 of 3

It is certified that error appears in the above-indentified patent and that said Letters Patent is hereby corrected as shown below:

> means for detecting a reflecting beam of light
>> that is reflected from the photographer's eye, said reflecting beam detecting means providing an output; and
>
> means for determining the direction in which said
>> eye gazes based on the output of said reflecting beam detecting means;
>
> wherein both of said beam guiding means and said
>> beam detecting means are mounted on an upper side of said camera and on an opposite side of said pentagonal prism from the eyepiece, said pentagonal prism being disposed therebetween.--

At column 39, line 27 (claim 90, line 1), change "ihn" to -- in --.

At column 40, line 34 (claim 93, line 1), change "eye detecting" to -- eye direction detecting --.

UNITED STATES PATENT AND TRADEMARK OFFICE
CERTIFICATE OF CORRECTION

PATENT NO. : 5,327,191
DATED : July 5, 1994
INVENTOR(S) : Osamu SHINDO et al.

It is certified that error appears in the above-indentified patent and that said Letters Patent is hereby corrected as shown below:

At column 40, line 50 (claim 94, line 1), change "92" to -- 93 --.

Signed and Sealed this

Twenty-first Day of November, 1995

Attest:

BRUCE LEHMAN

*Attesting Officer*    *Commissioner of Patents and Trademarks*